(12) United States Patent
Ding

(10) Patent No.: US 12,336,706 B2
(45) Date of Patent: Jun. 24, 2025

(54) ARTICULATION MECHANISM AND SURGICAL STAPLER

(71) Applicant: TOUCHSTONE INTERNATIONAL MEDICAL SCIENCE CO., LTD., Suzhou (CN)

(72) Inventor: Shuicheng Ding, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 0 days.

(21) Appl. No.: 18/669,854

(22) Filed: May 21, 2024

(65) Prior Publication Data

US 2024/0299028 A1  Sep. 12, 2024

Related U.S. Application Data

(63) Continuation of application No. PCT/CN2022/133654, filed on Nov. 23, 2022.

(30) Foreign Application Priority Data

Nov. 23, 2021 (CN) .......................... 202111394409.2
Nov. 23, 2021 (CN) .......................... 202111396060.6
Nov. 23, 2021 (CN) .......................... 202111396072.9
Nov. 23, 2021 (CN) .......................... 202122886676.3
Nov. 23, 2021 (CN) .......................... 202122886951.1
Nov. 23, 2021 (CN) .......................... 202122888036.6

(51) Int. Cl.
*A61B 17/072* (2006.01)
*A61B 17/00* (2006.01)

(52) U.S. Cl.
CPC .. *A61B 17/072* (2013.01); *A61B 2017/00367* (2013.01); *A61B 2017/00862* (2013.01)

(58) Field of Classification Search
CPC .................................................. A61B 17/072
See application file for complete search history.

(56) References Cited

U.S. PATENT DOCUMENTS

2005/0006434 A1* 1/2005 Wales .............. A61B 17/07207
227/19
2011/0062211 A1* 3/2011 Ross ...................... A61B 17/00
227/175.1

\* cited by examiner

*Primary Examiner* — Nathaniel C Chukwurah
(74) *Attorney, Agent, or Firm* — Westbridge IP LLC

(57) ABSTRACT

Disclosed are an articulation mechanism and a surgical stapler. The articulation mechanism includes: a gear assembly including a driving gear and at least one driven gear. The driving gear includes a first teeth portion, and the driven gear includes a second teeth portion engaged with the first teeth portion and a first mating portion; at least one articulation rod including a second mating portion and an articulation piece mating portion cooperated with the first mating portion, so that when the driven gear rotates, the driven gear drives the articulation piece mating portion of the articulation rod to move axially; at least one articulation piece extending axially and connected to the articulation piece mating portion. The mechanism can drive the head assembly to rotate relative to the instrument body of the stapler.

20 Claims, 23 Drawing Sheets

ARTICULATION MECHANISM AND SURGICAL STAPLER

CROSS-REFERENCE TO RELATED APPLICATIONS

This application is a continuation of International Application No. PCT/CN2022/133654, filed on Nov. 23, 2022, which claims priority to Chinese Patent Applications No. CN202111396072.9, CN202122888036.6, CN202122886951.1, CN202111396060.6, CN202111394409.2, and CN202122886676.3, filed on Nov. 23, 2021. All of the aforementioned applications are incorporated herein by reference in their entireties.

TECHNICAL FIELD

The present disclosure relates to surgical instruments' technology, more particularly, to an articulation mechanism and a surgical stapler.

BACKGROUND

In the prior art, the surgical stapler generally includes an instrument platform, a movable handle rotatably connected to the instrument platform and a head assembly cooperated with the instrument platform. The instrument body includes a firing assembly. The head assembly includes a cartridge assembly and an anvil arranged relative to each other. During surgery, two sections of tissue that need to be anastomosed are placed between the anvil and a cartridge of the cartridge assembly, a distance between the anvil and the cartridge is adjusted to gradually clamp the tissue, and then the movable handle drives the firing assembly to force the staples towards the anvil, so that two sections of tissue are anastomosed.

To meet the needs of more surgical scenarios, the head assembly needs to be able to be adjusted to various angles relative to the instrument platform. Therefore, an articulation mechanism is provided between the instrument body and the head assembly. The articulation mechanism includes an articulation piece having a distal end connected to the head assembly. When the articulation piece is driven to move in an axial direction of the stapler, the distal end of the articulation piece drives the head assembly to rotate clockwise or counterclockwise relative to the instrument body.

The existing articulation mechanism generally has a complex structure and the angle of rotation is difficult to be adjusted. During use, the head assembly may rotate uncontrollably, the angle of rotation of the head assembly will be uncontrollable, and the head assembly of the stapler will be unable to be accurately positioned, therefore the surgical effect is affected.

SUMMARY

To solve the problem in the prior art, the present disclosure aims to provide an articulation mechanism and a surgical stapler, to rotate the head assembly of the stapler relative to the instrument platform simply and conveniently, and the angle of rotation of the head assembly can be adjusted by gear engagement.

In the present disclosure, an articulation mechanism used for a surgical stapler is provided, including: a gear assembly including a driving gear and at least one driven gear, wherein the driving gear includes a first teeth portion, and the driven gear includes a second teeth portion configured to be engaged with the first teeth portion and a first mating portion; at least one articulation rod including a second mating portion and an articulation piece mating portion, wherein the second mating portion is configured to cooperate with the first mating portion, so that when the driven gear rotates, the driven gear drives the articulation piece mating portion of the articulation rod to move in an axial direction of the stapler; at least one articulation piece configured to extend in the axial direction and be connected to the articulation piece mating portion of the articulation rod.

In some embodiments, the mechanism further includes a housing configured to receive the gear assembly; wherein one of a first inner surface of the housing and the driving gear is provided with a support portion, and the other is provided with a sliding slot; wherein the support portion is configured to be rotatably located in the sliding slot.

In some embodiments, the first mating portion is located on a side of the second teeth portion facing the first inner surface of the housing.

In some embodiments, the support portion is annular or arc-shaped, and the sliding slot is annular or arc-shaped; wherein the sliding slot and the first teeth portion are coaxially arranged.

In some embodiments, the mechanism further includes a housing configured to receive the gear assembly; wherein the driven gear further includes a third mating portion, and an inner surface of the housing is provided with a fourth mating portion configured to cooperate with the third mating portion, so that the driven gear is rotatable relative to the housing.

In some embodiments, one of the third mating portion and the fourth mating portion includes a rotation shaft of the driven gear, and the other includes a fixing hole; wherein the rotation shaft is configured to be at least partially rotatably located in the fixing hole.

In some embodiments, the first mating portion is an eccentric wheel portion, and the second mating portion is provided with a fifth mating portion; wherein the eccentric wheel portion is configured to be at least partially located in the fifth mating portion.

In some embodiments, an outer contour of the eccentric wheel portion is circular or arc-shaped, and the fifth mating portion is a waist-shaped portion; wherein two straight edges of the waist-shaped portion are configured to extend in a transverse direction of the stapler.

In some embodiments, the mechanism includes two driven gears, two articulation rods and two articulation pieces; wherein the two articulation rods are symmetrically arranged relative to the axial direction, and each of the two articulation rods is respectively connected to one of the two articulation pieces; wherein when the driving gear rotates, the two articulation rods move in opposite directions.

In some embodiments, in an initial state, a central axis of the eccentric wheel portion of each driven gear is configured to be located outside or inside of the rotation shaft of corresponding driven gear.

In some embodiments, the articulation piece mating portion is a bulge or a groove arranged on an inner side of the second mating portion; wherein a proximal side of the articulation piece is provided with a hole or a bulge configured to cooperate with the articulation piece mating portion.

In some embodiments, the bulge or the groove is arranged at a center position of the articulation rod in the axial direction.

In some embodiments, an inner surface of the second mating portion is a plane parallel to the axial direction.

In some embodiments, the driven gear is configured to be located at a proximal side of the driving gear.

In some embodiments, the rotation shaft of each driven gear is parallel to a central axis of the driving gear; wherein a distance from the rotation shaft of one driven gear to the central axis of the driving gear is the same as a distance from the rotation shaft of the other driven gear to the central axis of the driving gear.

In some embodiments, a first inner surface of the housing is provided with at least one guiding slot configured to extend in the axial direction; wherein the articulation rod further includes at least one guiding portion configured to be located in the guiding slot and limited by the guiding slot to be movable only in the axial direction.

In some embodiments, the articulation rod includes two guiding portions; wherein in a transverse direction of the stapler, the two guiding portions are respectively connected to center portions of a distal surface and a proximal surface of the second mating portion.

In some embodiments, the driving gear further includes an operating portion; wherein a second inner surface of the housing is provided with a receiving hole, and the operating portion is configured to pass through the receiving hole and be exposed outside the housing.

In some embodiments, the mechanism further includes a housing including a first inner surface and a second inner surface, wherein a receiving cavity is configured to be formed between the first inner surface and the second inner surface; a fixing member configured to be fixedly located in the receiving cavity; wherein the fixing member includes a third surface facing the first inner surface and a fourth surface facing the second inner surface; wherein the gear assembly is configured to be at least partially located between the fourth surface and the second inner surface of the housing, and the gear assembly is rotatable relative to the fixing member.

In some embodiments, a first fixing portion is provided on a side of the fixing member facing the driving gear, and a second fixing portion is provided on a side of the driving gear facing the fixing member; wherein the first fixing portion and the second fixing portion are configured to form embedded connection, and the driving gear is rotatable relative to the first fixing portion.

In some embodiments, the driving gear further includes an operating portion configured to be located on a side of the first teeth portion facing the second inner surface of the housing; wherein the first fixing portion is provided on a side of the first teeth portion facing the first inner surface of the housing; wherein the first mating portion is configured to be located on a side of the second teeth portion facing the first inner surface of the housing; wherein the first teeth portion and the second teeth portion are configured to be located between the fourth surface and the second inner surface of the housing.

In some embodiments, the articulation rod is configured to be located between the third surface of the fixing member and the first inner surface of the housing; wherein the fixing member is provided with a through bore, and the first mating portion of the driven gear is configured to pass through the through bore to be engaged with the second mating portion of the articulation rod.

In some embodiments, one of the first fixing portion and the second fixing portion is a fixing column and the other is a groove; wherein the fixing column and the groove are configured to be coaxial and form embedded connection.

In some embodiments, the fixing member includes a first support portion for the driving gear; wherein at least a part of the first support portion and at least a part of the first inner surface of the housing form embedded connection; and/or, wherein the fixing member includes at least one second support portion for the driven gear; wherein at least a part of the second support portion and at least a part of the first inner surface of the housing form embedded connection.

In some embodiments, a receiving groove is provided on a side of the fixing member facing the first inner surface of the housing, and a limit portion is provided at a position of the housing relative to the receiving groove; wherein the receiving groove and the limit portion are configured to enclose a channel in the axial direction for receiving an elongated body.

In some embodiments, the gear assembly includes two driven gears, the fixing member includes two support portions configured to respectively support the two driven gears, and a channel configured to extend in the axial direction is formed between the two support portions.

In some embodiments, the second inner surface is provided with at least one limit member, and the limit member is configured to block movement of the support portions in the axial direction.

In some embodiments, the mechanism further includes at least one locking member provided with a locking portion; wherein when the gear assembly is not under external force, the locking portion is engaged with the gear assembly to block the driving gear and/or the driven gear from rotating, and when the gear assembly is driven to rotate under external force, the gear assembly drives the locking portion to move from the gear assembly, so that the locking portion no longer blocks the gear assembly from rotating.

In some embodiments, at least a part of the locking member is elastic.

In some embodiments, the first teeth portion includes a plurality of driving gear teeth, and the locking portion includes two inclined guiding surfaces or an arc surface; wherein when the locking portion is engaged with the first teeth portion, the guiding surfaces or the arc surface of the locking portion are at least partially in a space between two adjacent driving gear teeth; or, the second teeth portion includes a plurality of driven gear teeth, the locking portion includes two inclined guiding surfaces or an arc surface; wherein when the locking portion is engaged with the second teeth portion, the guiding surfaces of the locking portion are at least partially in a space between two adjacent driven gear teeth, and the two guiding surfaces are respectively located relative to side surfaces of the two adjacent driven gear teeth, or the arc surface of the locking portion is at least partially in a space between two adjacent driven gear teeth.

In some embodiments, the locking member is a rod configured to extend parallel to a central axis of the driving gear and/or a central axis of the driven gear.

In some embodiments, the mechanism further includes a housing and a fixing member, wherein the housing includes a receiving cavity configured to receive the gear assembly, the fixing member and the articulation rod; wherein the gear assembly is fixed to the housing through the fixing member; wherein the locking member further includes a connecting portion, and at least a part of the locking portion is configured to be connected to the fixing member through the connecting portion.

In some embodiments, the fixing member includes a first support portion for the driving gear and at least one second support portion for the driven gear, the first support portion is configured to be located between the driving gear and a first inner surface of the housing, the second support portion is configured to be located between the driven gear and the first inner surface of the housing; wherein the connecting portion of the locking member is configured to be connected to the first support portion and/or the second support portion.

In some embodiments, the mechanism includes two locking members; wherein the gear assembly includes two driven gears, the two locking members are respectively arranged between two second support portions and the first support portion; wherein the connecting portion of each locking member is configured to be connected to the first support portion through a first connecting arm; wherein the connecting portion of each locking member is configured to be connected to one second support portion through a second connecting arm.

In some embodiments, the first connecting arm is perpendicular to the second connecting arm.

The present disclosure further provides a surgical staple including the above articulation mechanism.

The articulation mechanism and the surgical stapler have the following advantages.

In the present disclosure, when the driving gear is driven to rotate, the driving gear drives the driven gear to rotate, and rotational movement of the driven gear is converted into axial movement of the articulation rod through the cooperation between the driven gear and the articulation rod, so that the articulation rod drives the articulation piece to move axially. Therefore, the head assembly is rotated relative to the instrument platform simply and conveniently. By adjusting direction and angle of rotation of the driving gear, direction and angle of rotation of the head assembly can be flexibly adjusted.

BRIEF DESCRIPTION OF THE DRAWINGS

By reading the detailed description of non-limiting embodiments with reference to the following drawings, other features, objectives, and advantages of the present disclosure will become more apparent.

DETAILED DESCRIPTION OF THE EMBODIMENTS

Figure 1:
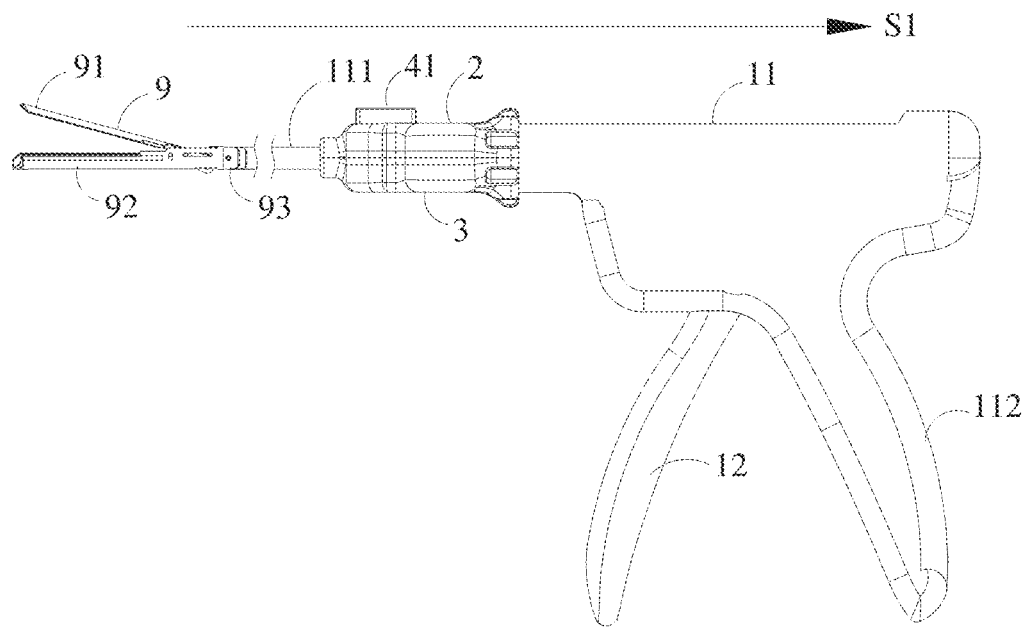
FIG. 1 is a structural schematic view of a surgical staple according to a first embodiment of the present disclosure.

The exemplary embodiments will be more comprehensively described by combining the drawings. However, the exemplary embodiments can be implemented in multiple forms and should not be limited to the embodiments described herein. On the contrary, providing these embodiments will make the present disclosure comprehensive and complete, and will comprehensively convey the concept of the exemplary embodiments to those skilled in the art. The same reference numbers in the drawings represent the same or similar structures, so repeated descriptions of them will be omitted.

The present disclosure provides an articulation mechanism and a surgical stapler including the same. The surgical stapler includes a head assembly, an instrument platform and the articulation mechanism arranged between the head assembly and the instrument platform. The articulation mechanism includes a driving gear, at least one driven gear, at least one articulation rod and at least one articulation piece. The driving gear includes a first teeth portion. The driven gear includes a second teeth portion engaged with the first teeth portion and a first mating portion. Therefore, when the operator rotates the driving gear, the driving gear can drive the driven gear to rotate.

The articulation rod includes a second mating portion and an articulation piece mating portion. The articulation piece extends in an axial direction of the stapler and is connected to the articulation piece mating portion of the articulation rod. The second mating portion is cooperated with the first mating portion. Therefore, when the driven gear rotates, the articulation piece mating portion of the articulation rod is driven to move axially, rotational movement of the driven gear is converted into axial movement of the articulation rod, the articulation piece is driven to move axially by the articulation rod, so that the head assembly of the stapler is rotated relative to the instrument platform simply and conveniently. Furthermore, in the present disclosure, direction and angle of rotation of the head assembly can be adjusted flexibly by adjusting direction and angle of rotation of the driving gear.

In the present disclosure, the driven gear refers to a gear having a first mating portion cooperated with the articulation rod, and the driving gear refers to a gear engaged with the driven gear, but it does not specifically mean that the driving gear must drive the driven gear to rotate. In an alternative embodiment, the driving gear may be rotated to drive the driven gear to rotate, or the driven gear may be rotated to drive the driving gear to rotate.

The structures of the articulation mechanisms in various embodiments of the present disclosure are described in detail below with reference to the drawings. It can be understood that the various specific embodiments are not intended to limit the protection scope of the present disclosure.

Figure 2:
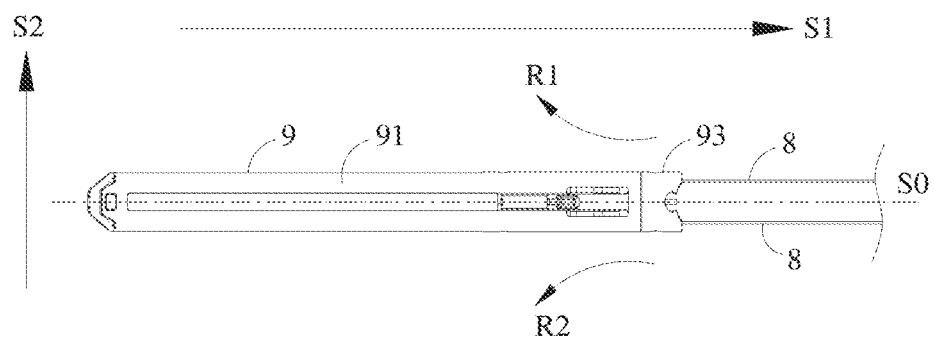
FIG. 2 is a structural schematic view of a head assembly cooperating with an articulation piece according to the first embodiment of the present disclosure.
Figure 3:
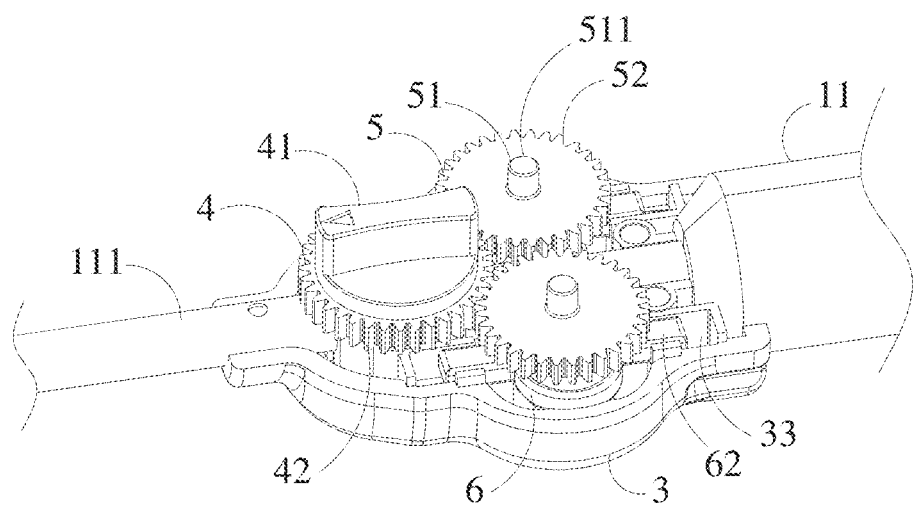
FIG. 3 is a structural schematic view of an articulation mechanism cooperating with an elongated body according to the first embodiment of the present disclosure.
Figure 4:
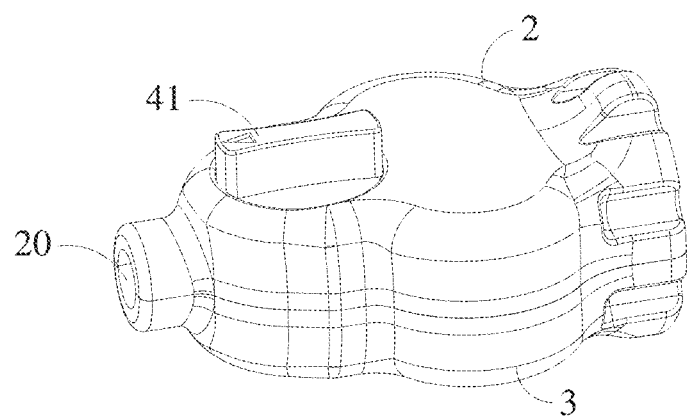
FIG. 4 is a structural schematic view of the articulation mechanism according to the first embodiment of the present disclosure.
Figure 5:
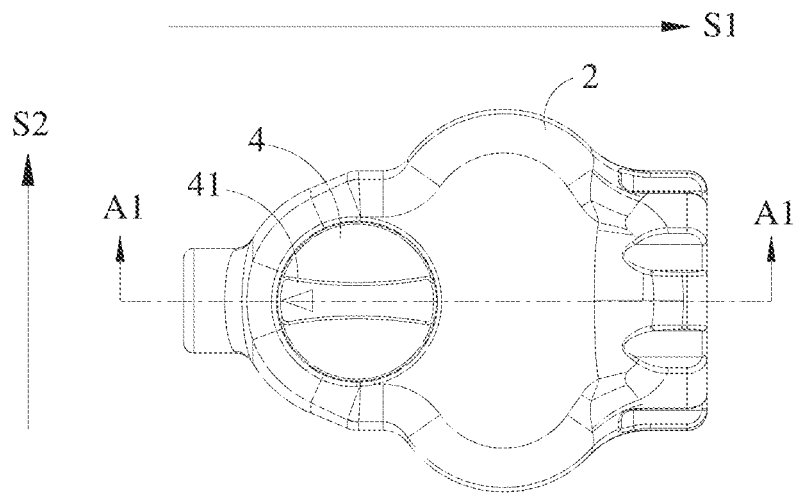
FIG. 5 is a top view of the articulation mechanism according to the first embodiment of the present disclosure.

As shown in FIGS. 1 and 2, in a first embodiment of the present disclosure, an articulation mechanism and a surgical stapler including the same are provided. The surgical stapler includes a head assembly 9, an instrument platform 11, a movable handle 12 rotatably connected to the instrument platform 11, and the articulation mechanism. The articulation mechanism is arranged between the head assembly 9 and the instrument platform 11. The instrument platform 11 includes a housing of the platform, a stationary handle 112 and an elongated body 111, and a distal end of the elongated body 111 is connected to the head assembly 9. The head assembly 9 includes an anvil 91 and a cartridge assembly 92 that are arranged relative to each other, and a connecting member 93 located at a proximal side of the anvil 91 and the cartridge assembly 92. The articulation mechanism includes two articulation pieces 8 at least partially located inside the elongated body 111. The elongated body 111 is omitted in FIG. 2 to illustrate the cooperation structure between the articulation pieces 8 and the head assembly 9. A distal side of the articulation piece 8 is connected to the connecting member 93. When the articulation piece 8 moves axially, the articulation piece 8 drives the head assembly 9 to rotate laterally relative to an axis S0 of the stapler. Specifically, in the perspective of FIG. 2, when the upper articulation piece 8 moves proximally and the lower articulation piece 8 moves distally, the head assembly 9 is rotated in the direction R1. When the upper articulation piece 8 moves distally and the lower articulation piece 8 moves proximally, the head assembly 9 is rotated in the direction R2.

Figure 6:
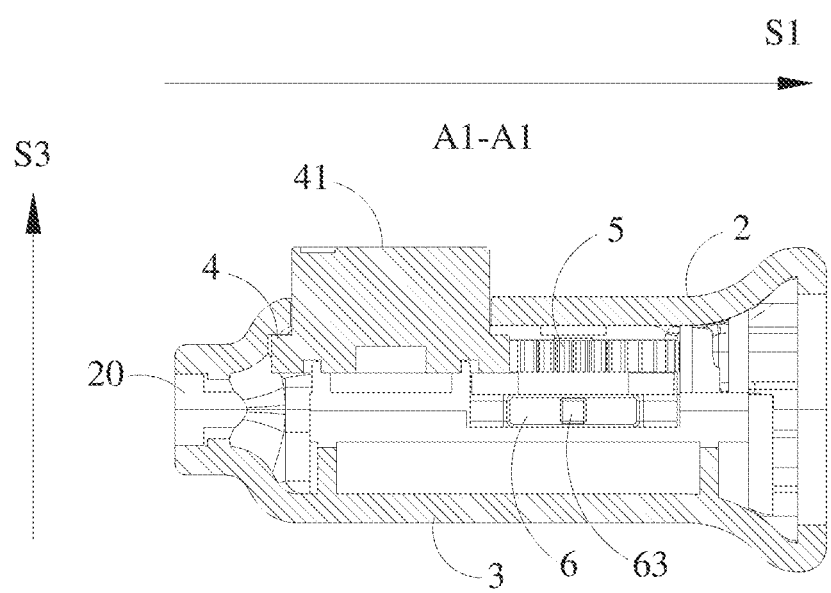
FIG. 6 is a cross-sectional view in A1-A1 direction of FIG. 5.
Figure 7:
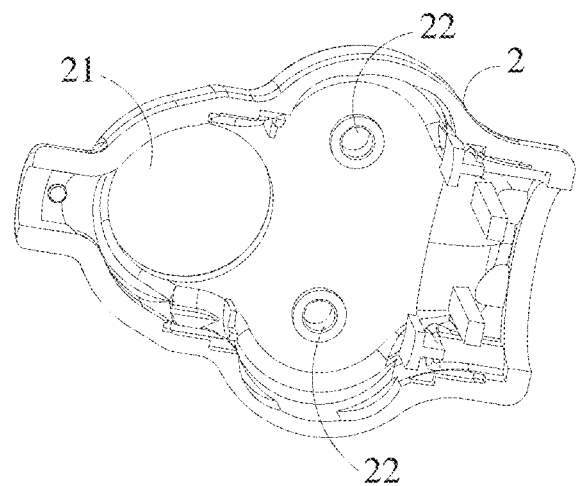
FIG. 7 is a structural schematic view of a second housing according to the first embodiment of the present disclosure.
Figure 8:
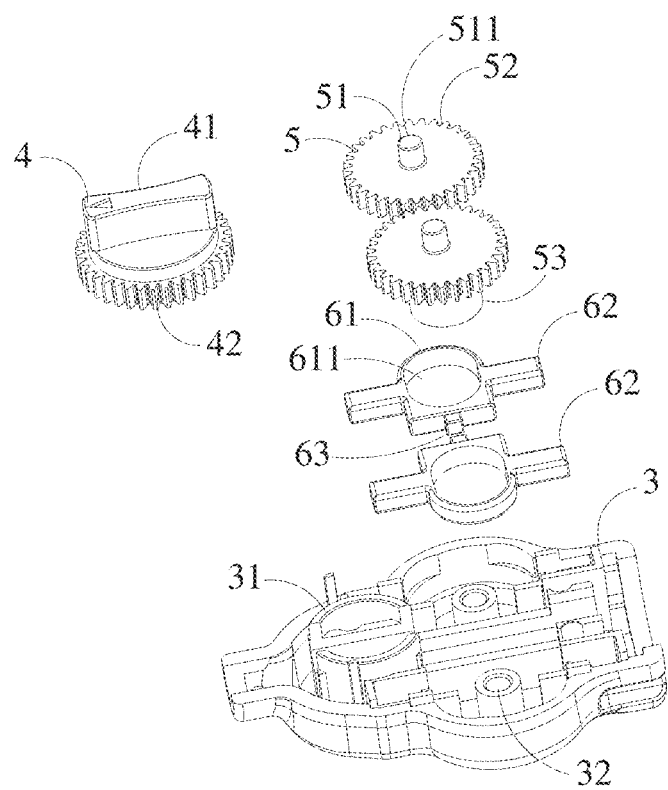
FIG. 8 and FIG. 9 are exploded views of the articulation mechanism omitting the second housing according to the first embodiment of the present disclosure.

In the present disclosure, the distal side and the proximal side are defined relative to the operator, the side close to the operator is the proximal side, and the side away from the operator, that is, the side close to the surgical site is the distal side. The extending direction of the axis of the stapler is the axial direction, that is, the direction from the distal side to the proximal side of the stapler, or from the proximal side to the distal side of the stapler. For example, in the perspective of FIG. 2, the distal side of the head assembly 9 is the left side, and the proximal side is the right side. The direction S1 is the direction from the distal side to the proximal side of the stapler. The direction S1 or the direction opposite to the S1 is defined as the axial direction of the stapler. The direction S2 in FIG. 2 is defined as the lateral direction of the stapler, that is, the width direction. The direction S3 in FIG. 6 is defined as the longitudinal direction of the stapler, that is, the height direction. The inside and outside of a member are defined relative to the axis of the stapler, the side close to the axis is the inside, and the side away from the axis is the outside. To describe the structures more clearly, "up" and "down" are described below based on the perspective in the drawings, but the descriptions should not be regarded as limitations of the present disclosure. In different embodiments, the relative position relationship of "upper" and "lower" can be interchanged.

As shown in FIG. 3 to FIG. 6, the articulation mechanism further includes a housing and a gear assembly. The gear assembly includes a driving gear 4 and at least one driven gear 5. The driving gear 4 and the driven gear 5 are received in a receiving cavity inside the housing. The articulation rod 6 is also located in the receiving cavity. In the perspective of FIG. 6, the housing includes a first housing 3 located at the bottom and a second housing 2 located at the top. The inner space of the second housing 2 and the first housing 3 forms a third channel 20 for receiving a part of the elongated body 111. The inner surface of the first housing 3 is the first inner surface of the housing, and the inner surface of the second housing 2 is the second inner surface of the housing. The driving gear 4 includes an operating portion and a first teeth portion 42, and a side wall of the first teeth portion 42 is at least partially provided with a first teeth surface. In this embodiment, the operating portion is an articulation lever 41 to be operated manually by an operator. In another embodiment, the driven gear 5 may include an operating portion, and the driven gear 5 is manually operated to drive the driving gear 4 to rotate. The driven gear 5 includes a second teeth portion 52, a side wall of the second teeth portion 52 is at least partially provided with a second teeth surface, and the first teeth surface is engaged with the second teeth surface. Therefore, when the operator operates the articulation lever 41 to rotate the driving gear 4, the driven gear 5 can be driven to rotate as the first teeth surface is engaged with the second teeth surface. In this embodiment, two driven gears 5 located at a proximal side of the driving gear 4 are provided. The two driven gears 5 are symmetrically arranged relative to the axis of the stapler, and central axes of the two driven gears 5 are parallel to a central axis of the driving gear 4. A distance from the central axis of one driven gear 5 to the central axis of the driving gear 4 is the same as a distance from the central axis of the other driven gear 5 to the central axis of the driving gear 4. The receiving cavity in the first housing 3 and the second housing 2 is shaped to fit the gear assembly.

As shown in FIGS. 7 to 10, the first mating portion is provided on a side of the second teeth portion 52 of the driven gear 5 facing the first housing 3. In this embodiment, the first mating portion is an eccentric wheel portion 53, and an outer contour of the eccentric wheel portion 53 is circular or arc-shaped. In other embodiments, the outer contour of the eccentric wheel portion 53 may also be in other shapes, such as a triangle or other kinds of polygons. The articulation mechanism further includes at least one articulation rod 6 received in the housing. In this embodiment, two articulation rods 6 corresponding to the driven gears 5 are provided. The two articulation rods 6 are symmetrically arranged relative to the axial direction of the stapler, and each articulation rod 6 is connected to an articulation piece 8 respectively. When the driving gear 4 rotates, movement directions of the two articulation rods 6 are opposite. The articulation rod 6 includes a second mating portion and an articulation piece mating portion 63. The articulation piece mating portion 63 of the articulation rod 6 is connected to the proximal side of the corresponding articulation piece 8. In this embodiment, the second mating portion is an eccentric wheel mating portion 61 cooperated with the eccentric wheel portion 53. Therefore, when the driven gear 5 rotates, the articulation piece mating portion 63 of the articulation rod 6 is driven to move axially, so that the rotational movement of the driven gear 5 is converted into the axial movement of the articulation rod 6. When the operator operates the articulation lever 41 to rotate the driving gear 4, the driving gear 4 drives the driven gears 5 to rotate as the first teeth surface is engaged with the second teeth surface. The driven gears 5 rotate to drive the articulation rods 6 to move axially, so that the articulation pieces 8 can be driven to move axially through the articulation rods 6. Therefore, the head assembly 9 can be rotated relative to the instrument platform 11 simply and conveniently. Furthermore, direction and angle of rotation of the head assembly 9 can be adjusted by adjusting direction and the angle of rotation of the driving gear 4.

Figure 9:
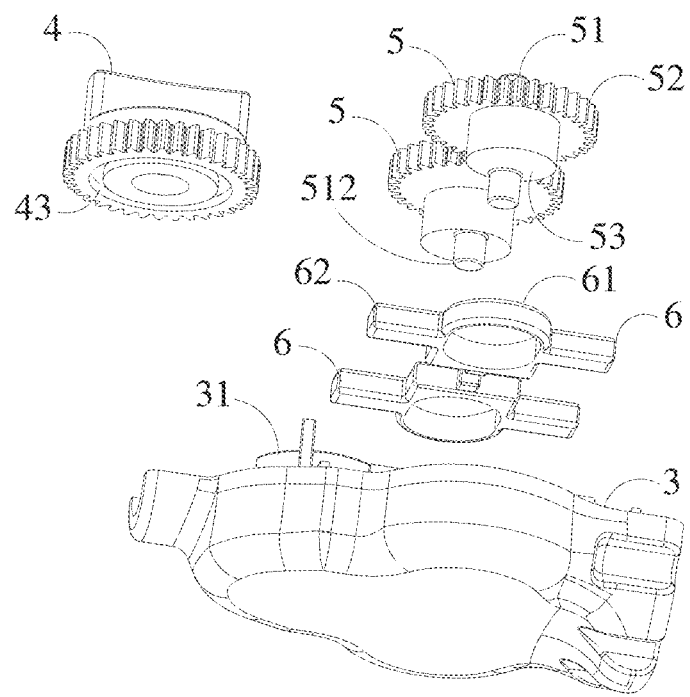
Figure 10:
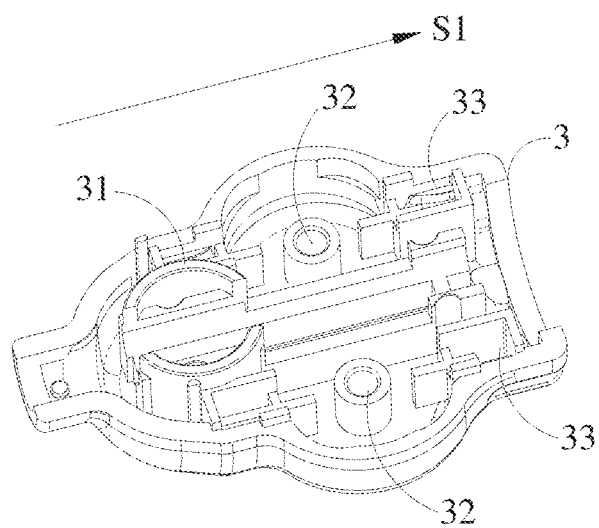
FIG. 10 is a structural schematic view of a first housing according to the first embodiment of the present disclosure.

As shown in FIGS. 7 to 10, a receiving hole 21 is provided on the surface of the second housing 2. The articulation lever 41 passes through the receiving hole 21 and is exposed outside the second housing 2. The inner surface of the first housing 3 is provided with a support portion 31 convex from the first inner surface, and a sliding slot 43 is provided on a side of the driving gear 4 facing the inner surface of the first housing 3. The support portion 31 is at least partially in the sliding slot 43, and the driving gear 4 is rotatable relative to the support portion 31. As shown in FIG. 9 and FIG. 10, the support portion 31 is arc-shaped, and the sliding slot 43 is annular. The support portion 31 and the sliding slot 43 are coaxially arranged and sized to fit each other. The sliding slot 43 is coaxially arranged with the first teeth portion 42, and a diameter of the sliding slot 43 is smaller than an outer diameter of the first teeth portion 42. As the support portion 31 is cooperated with the sliding slot 43, the central axis of the driving gear 4 is prevented from moving axially and laterally. In another alternative embodiment, the support portion may be an annular portion coaxially arranged with an annular sliding slot and sized to fit the sliding slot. In another alternative embodiment, both the support portion and the sliding slot are arc-shaped, and a length of the arc-shaped slide groove is greater than a length of the arc-shaped support portion, so that the support portion is rotatable in the sliding slot in a circumferential direction. In another alternative embodiment, a sliding slot may be provided on the inner surface of the first housing 3, and a support portion may be provided on the side of the driving gear 4 facing the inner surface of the first housing 3, the support portion is located in the sliding slot, and the support portion is rotatable relative to the sliding slot, so that the driving gear 4 is rotatable relative to the first housing 3.

As shown in FIGS. 7 to 10, in this embodiment, the driven gear 5 further includes a rotation shaft 51. The inner surface of the second housing 2 is provided with a second fixing hole 22, and the inner surface of the first housing 3 is provided with a first fixing hole 32. A first end 511 is in the second fixing hole 22, and a second end 512 of the rotation shaft 51 is in the first fixing hole 32. The rotation shaft 51 passes through both the second teeth portion 52 and the eccentric wheel portion 53. Both the second teeth portion 52 and the eccentric wheel portion 53 are rotatable around the rotation shaft 51. Here, the second teeth portion 52 and the eccentric wheel portion 53 being rotatable around the rotation shaft 51 can be realized in two ways. In one way, the rotation shaft 51 is non-rotatably fixed to both the second fixing hole 22 and the first fixing hole 32; both the second teeth portion 52 and the eccentric wheel portion 53 are rotatable relative to the rotation shaft 51. In the other way, the rotation shaft 51 is rotatably located in both the second fixing hole 22 and the first fixing hole 32; both the first teeth portion 42 and the eccentric wheel portion 53 are non-rotatably jacketed outside the rotation shaft 51, so that the first teeth portion 42, the eccentric wheel portion 53 and the rotation shaft 51 are all rotatable around the axis of the rotation shaft 51.

As shown in FIGS. 9 and 10, the first inner surface of the housing is provided with guiding slots 33 extending in the axial direction, and the articulation rod 6 further includes at least one guiding portion 62. The guiding portion 62 is in the guiding slot 33 and limited by the guiding slot 33 to be movable only in the axial direction. When the driving gear 4 rotates, the articulation rod 6 is ensured to be movable only in the axial direction and not movable in the lateral direction. Specifically, in this embodiment, the articulation rod 6 includes two guiding portions 62 respectively located on a distal side and a proximal side of the eccentric wheel mating portion 61, and each guiding portion 62 is in a shape of a strip extending in the axial direction of the stapler.

Figure 11:
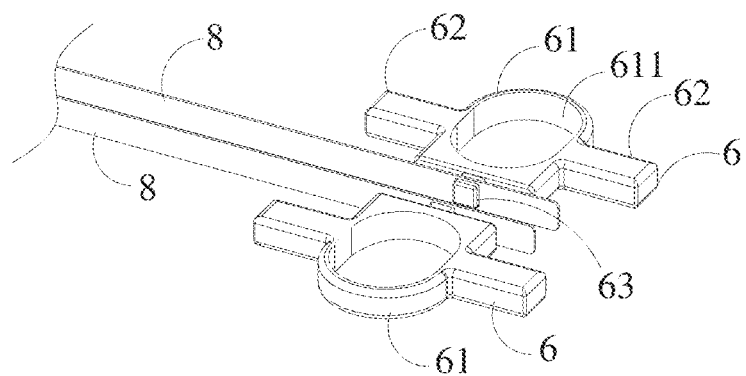
FIG. 11 is a structural schematic view of articulation rods cooperating with the articulation pieces according to the first embodiment of the present disclosure.
Figure 12:
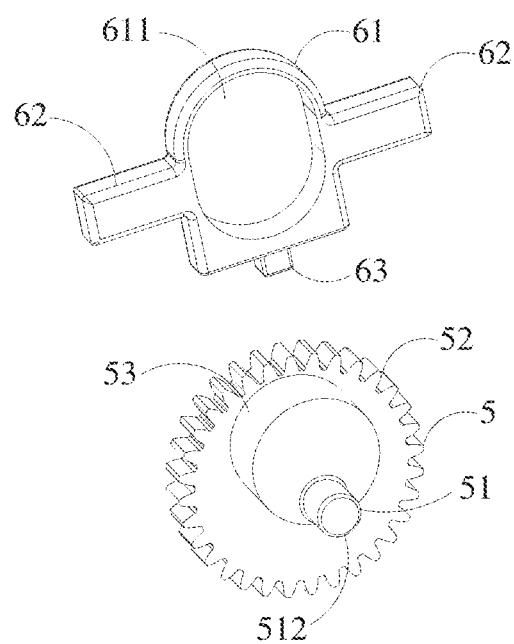
FIG. 12 is an exploded view of the articulation rod cooperating with a driven gear according to the first embodiment of the present disclosure.

As shown in FIG. 11 and FIG. 12, the rotation shaft 51 passes through a center of the second teeth portion 52. However, the eccentric wheel portion 53 is eccentrically arranged relative to the rotation shaft 51, that is, a distance from a center of the rotation shaft 51 to a central axis O1 of the eccentric wheel portion 53 is a first distance d1 shown in FIG. 13. A fifth mating portion is provided in the eccentric wheel mating portion 61 of the articulation rod 6. The fifth mating portion is a mating hole, and the eccentric wheel portion 53 is at least partially in the mating hole. In another alternative embodiment, the fifth mating portion of the articulation rod 6 can be a mating groove, and the eccentric wheel portion 53 is at least partially in the mating groove. The eccentric wheel portion 53 cooperates with the mating groove or the mating hole to drive the articulation rod 6 to move axially.

As shown in FIGS. 11 and 12, the articulation piece mating portion 63 is a convex portion arranged on an inner side of the eccentric wheel mating portion 61, a hole cooperated with the convex portion is arranged on a proximal side of the articulation piece 8, and the convex portion is embedded in the hole on the proximal side of the articulation piece 8. Each side surface of the convex portion is selectively a right-angled surface, so that the convex portion is stably cooperated with the articulation piece 8 and the convex portion is prevented from accidentally separating from the hole. Selectively, the convex portion is arranged at a center portion of the articulation rod 6 in the axial direction, that is, a distance from a center of the convex portion to a distal end of the articulation rod 6 is the same as a distance from the center of the convex portion to a proximal end of the articulation rod 6. When the articulation rod 6 drives the articulation piece 8 to move axially, the articulation rod 6 is further prevented from being moved laterally under external force. In another alternative embodiment, the articulation piece mating portion 63 may be a groove arranged on the inner side of the eccentric wheel mating portion 61, and the proximal side of the articulation piece 8 is provided with a convex portion embedded in the groove, and the groove is selectively arranged at the center position of the articulation rod 6 in the axial direction. In this embodiment, the inner surface of the eccentric wheel mating portion 61 is a plane surface parallel to the axial direction of the stapler to better fit the sheet shape of the articulation piece 8.

Figure 13:
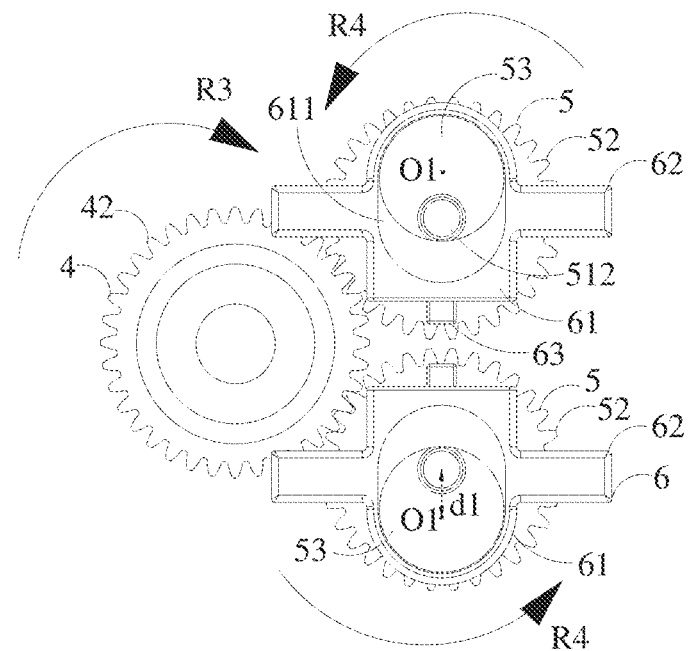
FIG. 13 and FIG. 14 are schematic views of the articulation mechanism driving the head assembly to rotate in direction R1 according to the first embodiment of the present disclosure.

As shown in FIG. 13, in the lateral direction of the stapler, the two guiding portions 62 are respectively connected to the center portion of the distal surface and the proximal surface of the eccentric wheel mating portion 61, so that the limiting force of the guiding slot 33 (shown in FIG. 3) on the guiding portion 62 acts more evenly on various positions of the articulation rod 6. Therefore, when the articulation rod 6 is moved axially, the articulation rod 6 is prevented from being moved laterally under an action of the rotational movement of the eccentric wheel portion 53. The mating hole of the eccentric wheel mating portion 61 is a waist-shaped hole 611 having a contour including two arc sides and two straight sides. A radius of the arc side is substantially the same as a radius of the eccentric wheel portion 53. The two straight sides of the waist-shaped hole 611 extend laterally. In another alternative embodiment, the shape of the mating hole is different from the waist shape shown in FIG. 13, and the shape needs to fulfill the requirement that when the eccentric wheel portion 53 rotates, the eccentric wheel mating portion 61 is driven by the eccentric wheel portion 53 to move axially.

FIG. 13 shows the cooperation of the driving gear 4, the driven gears 5 and the articulation rod 6 in the initial state. In the initial state, the central axes O1 of the eccentric wheel portions 53 of the two driven gears 5 are both located outside the corresponding rotation shafts 51. Therefore, when the driving gear 4 drives the driven gears 5 to rotate, the two driven gears 5 can drive the two articulation rods 6 to move in opposite directions. In another alternative embodiment, in the initial state, the central axes of the eccentric wheel portions 53 of the two driven gears 5 may be both located on the inner side of the corresponding rotation shafts 51.

Figure 14:
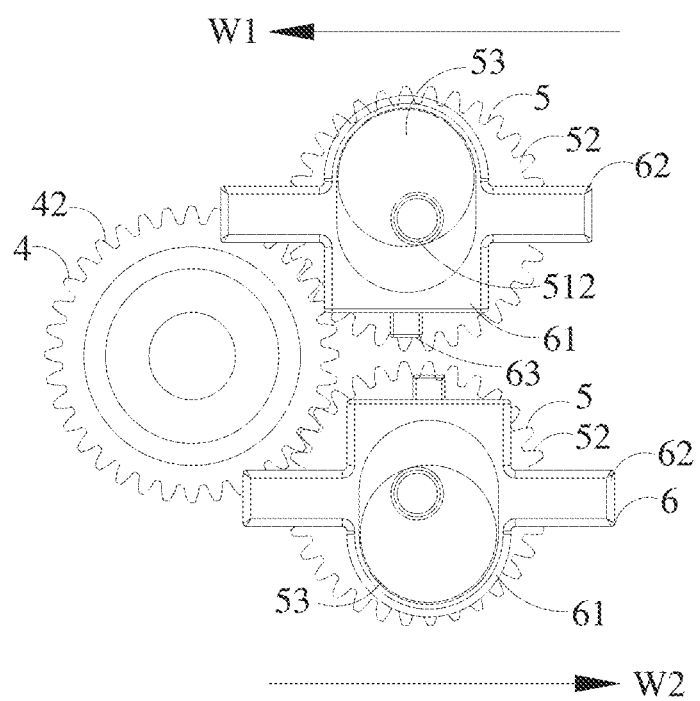

As shown in FIG. 13, in the initial state, when the driving gear 4 is operated to rotate in direction R3, the driving gear 4 drives the driven gears 5 to rotate in direction R4, and then the mechanism enters the state shown in FIG. 14. FIG. 14 shows a state in which the driving gear 4 rotates 15° in the direction R3 compared to the state in FIG. 13. The upper articulation rod 6 shown in FIG. 14 moves in direction W1 compared to the state in FIG. 13, that is, the upper articulation rod 6 moves distally. The lower articulation rod 6 moves in direction W2 compared to the state in FIG. 13, that is, the lower articulation rod 6 moves proximally. Therefore, the head assembly 9 is rotated in the direction R1 shown in FIG. 2.

Figure 15:
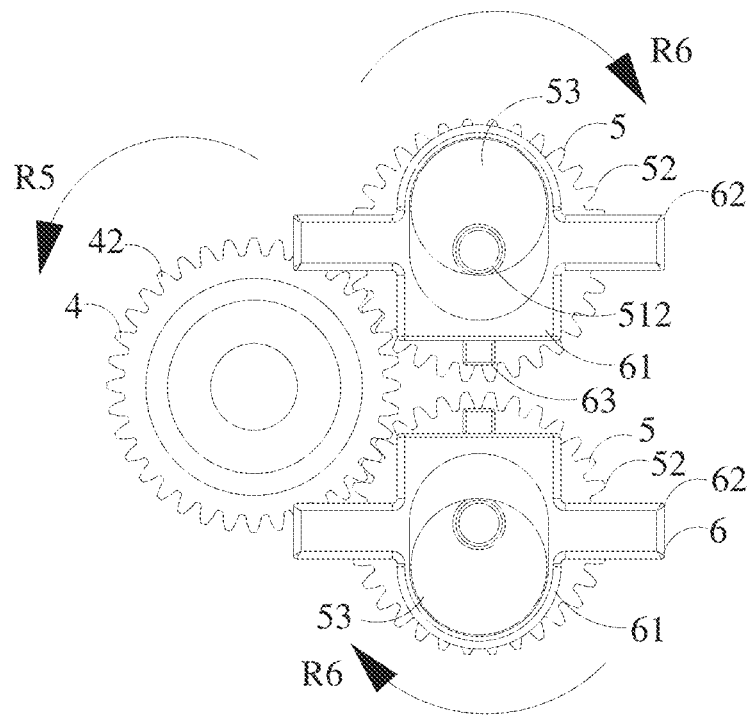
FIG. 15 and FIG. 16 are schematic views of the articulation mechanism driving the head assembly to rotate in direction R2 according to the first embodiment of the present disclosure.
Figure 16:
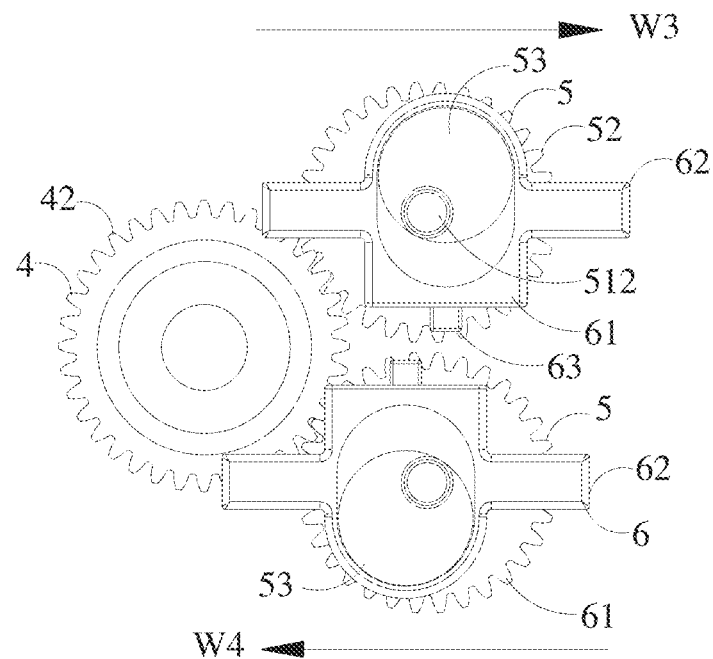

As shown in FIG. 15, in the initial state, when the driving gear 4 is operated to rotate in direction R5, the driving gear 4 drives the driven gears 5 to rotate in direction R6, then the mechanism enters the state shown in FIG. 16. FIG. 16 shows a state in which the driving gear 4 is rotated 30° in the R5 direction compared to the state in FIG. 15. The upper articulation rod 6 shown in FIG. 16 moves in direction W3 compared to the state in FIG. 15, that is, the upper articulation rod 6 moves proximally. The lower articulation rod 6 moves in W4 direction compared to the state in FIG. 15, that is, the lower articulation rod 6 moves distally. Therefore, the head assembly 9 is rotated in the direction R2 shown in FIG. 2. By comparing FIG. 14 and FIG. 16, when the driving gear 4 rotates in different directions, the head assembly 9 rotates in different directions. Furthermore, when the angle of rotation of the driving gear 4 is changed, the movement displacement of the articulation rod 6 is changed, so that the angle of rotation of the head assembly 9 is also changed. The greater the angle of rotation of the driving gear 4 is, the greater the movement displacement of the articulation rod 6 is, and the greater the angle of rotation of the head assembly 9 is. Therefore, the direction of rotation and angle of rotation of the head assembly 9 can be flexibly adjusted.

FIGS. 17 to 28 show the structure of an articulation mechanism according to a second embodiment of the present disclosure. The second embodiment is different from the first embodiment in that the mechanism of the second embodiment further includes a fixing member, and the gear assembly is cooperated with the housing in a different way.

The other parts of the stapler in this embodiment have the same structures as those in the first embodiment, and the principle of the gear assembly driving the articulation piece is the same, so the second embodiment is introduced below with reference to FIGS. 1, 2, 13 to 16 and 17 to 28.

As shown in FIGS. 17 to 20, the articulation mechanism includes a housing, a gear assembly, articulation rods 6, a fixing portion 7 and articulation pieces 8. The housing includes a first housing 3 and a second housing 2. The gear assembly, the articulation rod 6 and the fixing member 7 are all received in a receiving cavity in the housing. The gear assembly includes a driving gear 4 and driven gears 5, and the driving gear 4 includes an operating portion and a first teeth portion 42. In this embodiment, the operating portion is an articulation lever 41 at least partially exposed outside the second housing 2. In another embodiment, an operating portion is provided on the driven gear 5, and the driven gear 5 is manually operated to drive the driving gear 4 to rotate. The driven gear 5 includes a second teeth portion 52, a first mating portion and a rotation shaft 51. The rotation shaft 51 passes through the second teeth portion 52 and the first mating portion. The articulation rod 6 includes a second mating portion and an articulation piece mating portion 63. The articulation piece mating portion 63 is connected to a proximal end of the articulation piece 8. The second mating portion is cooperated with the first mating portion.

In this embodiment, two articulation rods 6 are provided corresponding to two articulation pieces 8, and the two articulation rods 6 are symmetrically arranged relative to the axial direction of the stapler. When the driving gear 4 rotates, the moving directions of the two articulation rods 6 are opposite. Two driven gears 5 are correspondingly provided, and the two driven gears 5 are located at the proximal side of the driving gear 4. The two driven gears 5 are symmetrically arranged relative to the axis of the stapler, and central axes of the two driven gears 5 are parallel to a central axis of the driving gear 4. A distance between the central axis of one driven gear 5 and the central axis of the driving gear 4 is the same as a distance between the central axis of the other driven gear 5 and the central axis of the driving gear 4. The receiving cavity in the first housing 3 and the second housing 2 is shaped to fit the shape of the gear assembly.

When the operator rotates the driving gear 4, the driven gear 5 can be driven to rotate as the first teeth portion 42 is engaged with the second teeth portion 52. As the first mating portion is cooperated with the second mating portion, the rotational movement of the driven gear 5 is converted into the axial movement of the articulation rod 6, and the articulation piece 8 is driven to move axially by the articulation rod 6, so that the head assembly 9 (shown in FIG. 1) is rotated relative to the instrument platform 11 (shown in FIG. 1) simply and conveniently. By adjusting the direction and the angle of rotation of the driving gear 4, the direction and the angle of rotation of the head assembly 9 can be flexibly adjusted.

Figure 17:
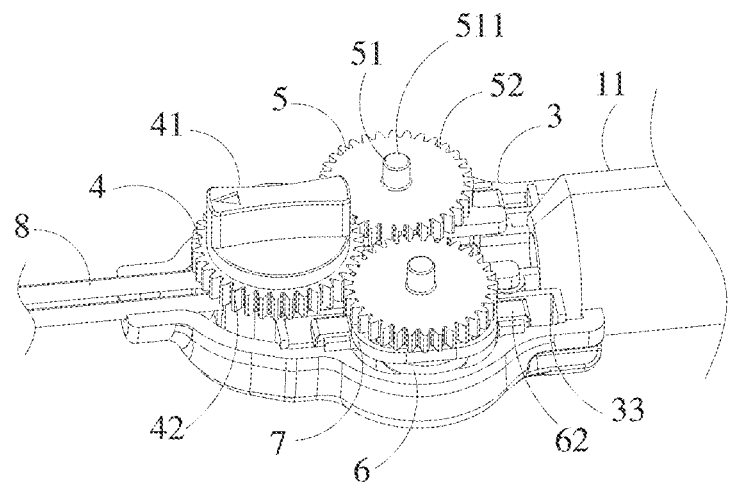
FIG. 17 is a structural schematic view of an articulation mechanism omitting a second housing and cooperating with an instrument platform of the stapler according to a second embodiment of the present disclosure.
Figure 18:
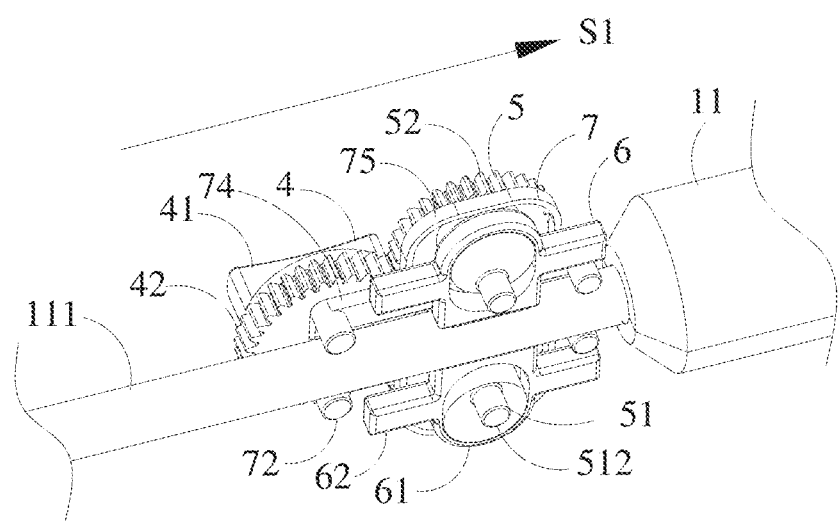
FIG. 18 is a structural schematic view of the articulation mechanism omitting a housing and cooperating with an instrument platform of the stapler according to the second embodiment of the present disclosure.

The housing includes a first inner surface and a second inner surface. The first inner surface and the second inner surface surround a receiving cavity. As shown in FIG. 1 and FIG. 17, in this embodiment, the first housing 3 is located at the bottom and the second housing 2 is located at the top, and a third channel 20 for the elongated body passing through is formed in the first housing 3 and the second housing 2. The first inner surface is the inner surface of the first housing 3, and the second inner surface is the inner surface of the second housing 2. A fixing member 7 is located between the gear assembly and the first inner surface, the gear assembly is fixed to the first inner surface through the fixing member 7. Both the driving gear 4 and the driven gear 5 are rotatable relative to the fixing member 7, so that the structural stability of the articulation mechanism is improved, unstable movement of the head assembly 9 during use due to instability of the gear assembly during use is prevented, and surgical effect is improved. As shown in FIG. 17 and FIG. 18, the fixing member 7 includes a third surface facing the first inner surface and a fourth surface facing the second inner surface. The gear assembly is at least partially located between the fourth surface of the fixing member 7 and the second inner surface. The articulation rod 6 is located between the third surface of the fixing member 7 and the first inner surface. The fixing member 7 and the articulation rod 6 are fixed relative to the housing in the height direction.

Figure 19:
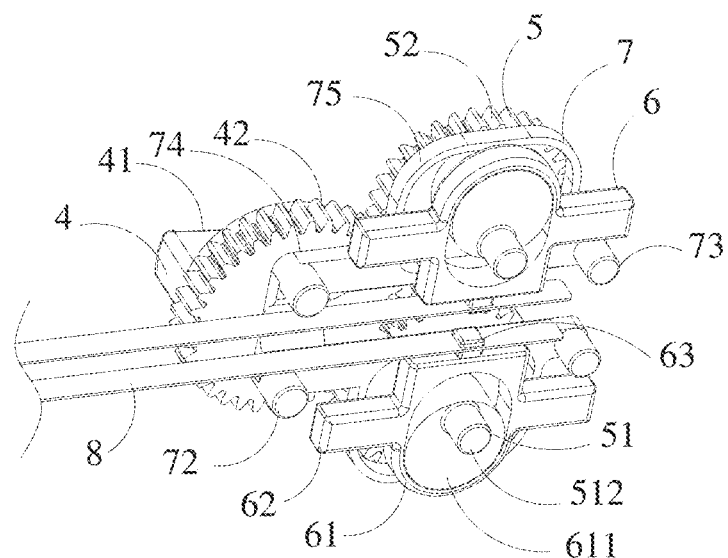
FIG. 19 is a structural schematic view of the articulation mechanism omitting the housing according to the second embodiment of the present disclosure.
Figure 20:
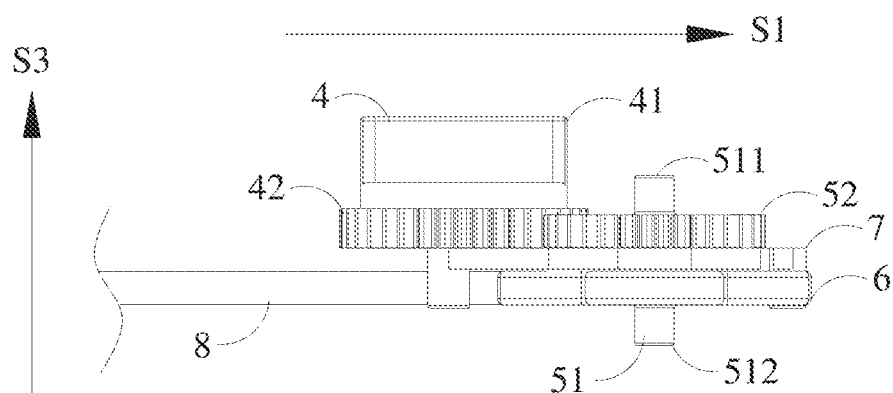
FIG. 20 is a front view of the articulation mechanism omitting the housing according to the second embodiment of the present disclosure.
Figure 21:
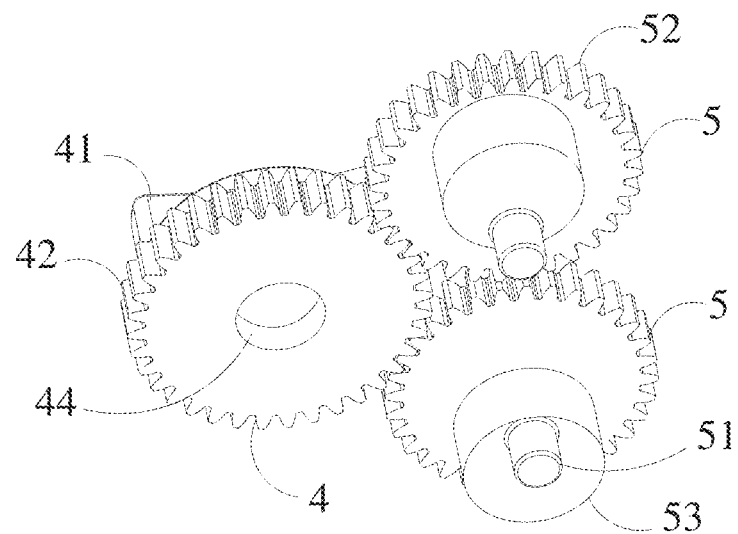
FIG. 21 is a structural schematic view of a gear assembly according to the second embodiment of the present disclosure.

As shown in FIGS. 19 to 21, the first mating portion is an eccentric wheel portion 53, and the second mating portion is an eccentric wheel mating portion 61 cooperated with the eccentric wheel portion 53. Therefore, when the driven gear 5 rotates, the articulation piece mating portion 63 of the articulation rod 6 is driven to move in the axial direction of the stapler, so that the rotational movement of the driven gear 5 is converted into the axial movement of the articulation rod 6. In this embodiment, an outer contour of the eccentric wheel portion 53 is circular or arc-shaped. In other embodiments, the outer contour of the eccentric wheel portion 53 may be in other shapes, such as a triangle or other kinds of polygons. The rotation shaft 51 passes through a center of the second teeth portion 52. However, the eccentric wheel portion 53 is eccentrically arranged relative to the rotation shaft 51, that is, a distance from a center of the rotation shaft 51 to a central axis O1 of the eccentric wheel portion 53 is a first distance d1 shown in FIG. 13. A third mating hole is provided in the eccentric wheel mating portion 61 of the articulation rod 6. The third mating hole is a waist-shaped hole 611, and the eccentric wheel portion 53 is at least partially in the waist-shaped hole 611. In other embodiments, the third mating hole may be changed to other shapes. In another alternative embodiment, a mating groove may be provided in the eccentric wheel mating portion 61 of the articulation rod 6, and the eccentric wheel portion 53 is at least partially in the mating groove.

As shown in FIGS. 17 and 19, the inner surface of the first housing 3 is provided with guiding slots 33 extending in the axial direction of the stapler, and the articulation rod 6 further includes at least one guiding portion 62. The position of the guiding portion 62 and the cooperation between the guiding portion 62 and the guiding slot 33 are the same as those in the first embodiment and are not described in detail here. As shown in FIG. 19, the articulation piece mating portion 63 is a convex portion arranged on an inner side of the eccentric wheel mating portion 61, a hole cooperated with the convex portion is arranged on a proximal side of the articulation piece 8, and the convex portion is embedded in the hole on the proximal side of the articulation piece 8. The selective cooperation structures between the articulation piece mating portion 63 and the articulation piece 8 are the same as those of the first embodiment and are not described in detail here.

In the second embodiment, the working principle of the articulation mechanism driving the head assembly to rotate in the direction R1 or the direction R2 relative to the instrument platform is the same as that described in the first embodiment with reference to FIGS. 13 to 16 and are not described in detail here.

Figure 22:
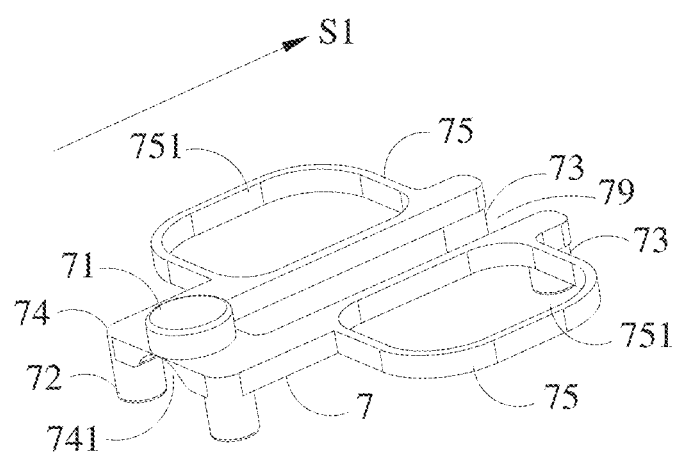
FIG. 22 is a structural schematic view of a fixing member according to the second embodiment of the present disclosure.
Figure 27:
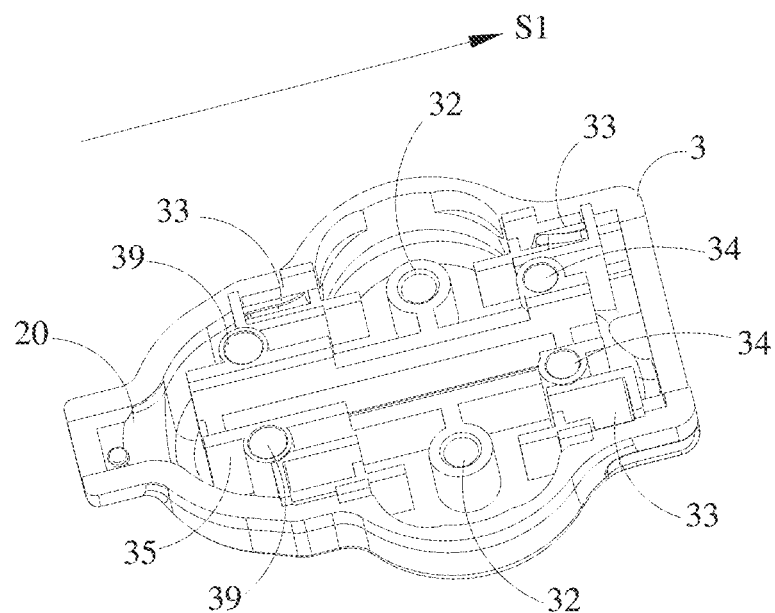
FIG. 27 is a structural schematic view of the first housing according to the second embodiment of the present disclosure.
Figure 28:
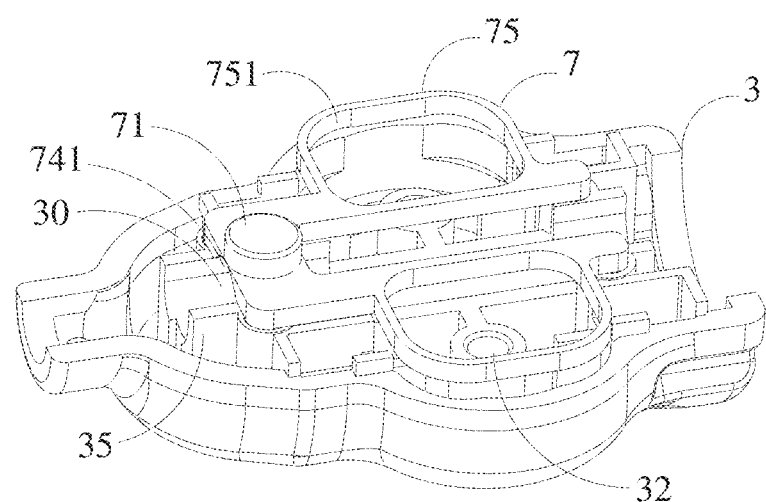
FIG. 28 is a structural schematic view of the fixing member cooperating with the first housing according to the second embodiment of the present disclosure.

The cooperation structure between the fixing member 7 and other members of the second embodiment is described in detail below with reference to FIG. 17, FIG. 21, and FIG. 22 to FIG. 28. As shown in FIG. 17 and FIG. 22, the fixing member 7 includes a first support portion 74 and two second support portions 75. The first support portion 74 is located between the driving gear 4 and the first inner surface of the housing. The second support portion 75 is located between the driven gear 5 and the first inner surface of the housing. The articulation rod 6 is located between the second support portion 75 and the first inner surface. A receiving groove 741 is provided on a side of the first support portion 74 facing the first inner surface of the housing. As shown in FIGS. 27 and 28, a limit portion 35 is provided at a position of the first inner surface corresponding to the receiving groove 741. The receiving groove 741 and the limiting portion 35 form a first channel 30 extending axially, and the elongated body jacketed on the articulation piece 8 passes through the first channel 30. A surface of the receiving groove 741 is selectively an arc surface, and a surface of the limit portion 35 is also selectively an arc surface. Therefore, the first channel 30 is cylindrical to better fit the outer surface of the cylindrical elongated body and better support the elongated body. As shown in FIG. 22, a second channel 79 extending axially is formed between the two second support portions 75, and a proximal end of the elongated body passes through the second channel 79.

Figure 23:
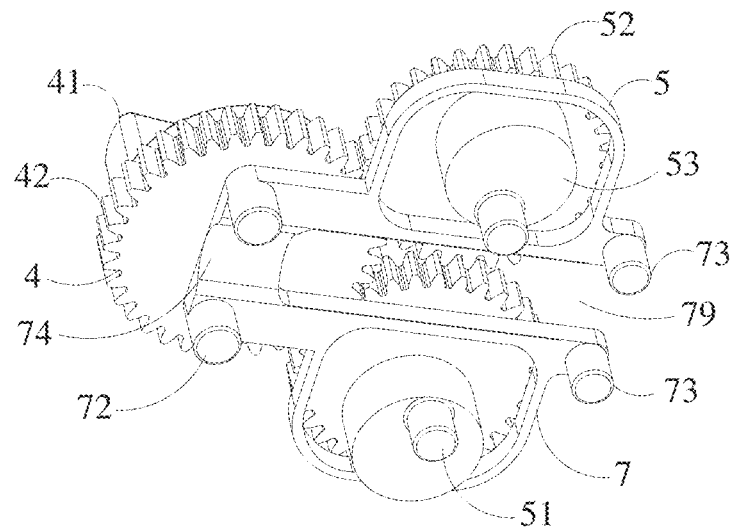
FIG. 23 is a structural schematic view of the gear assembly cooperating with a fixing member according to the second embodiment of the present disclosure.
Figure 24:
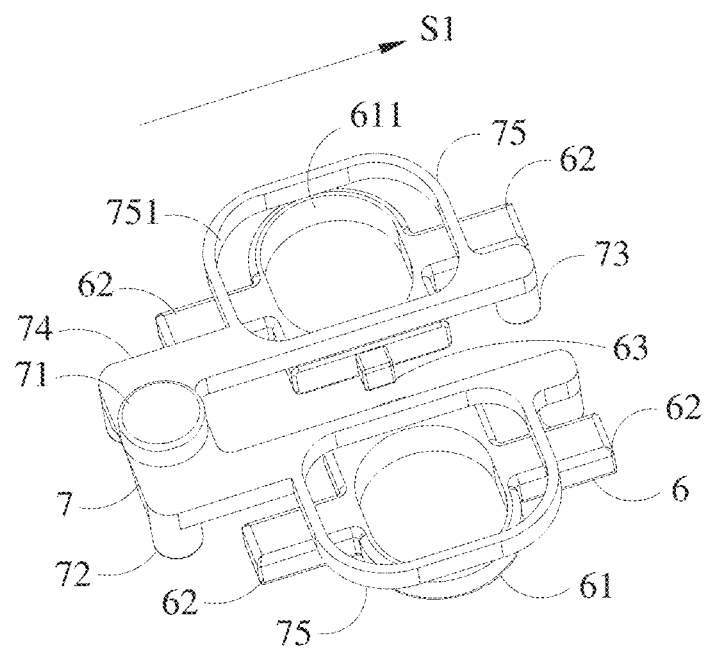
FIG. 24 is a structural schematic view of the fixing member cooperating with articulation rods according to the second embodiment of the present disclosure.

As shown in FIGS. 22 and 23, the second support portion 75 of the fixing member 7 is provided with a through bore 751, the rotation shaft 51 of the driven gear 5 passes through the through bore 751. The eccentric wheel portion 53 of the driven gear 5 passes through the through bore 751 and then cooperates with the eccentric wheel mating portion 61 of the articulation rod 6. Therefore, in this embodiment, both the first teeth portion 42 of the driving gear 4 and the second teeth portion 52 of the driven gear 5 are arranged between the fourth surface of the fixing member 7 and the second inner surface of the housing. As the articulation rod 6 is located between the third surface of the fixing member 7 and the first inner surface of the housing, the eccentric wheel portion 53 passes through the through bore 751 of the fixing member 7 and then cooperates with the articulation rod 6. As shown in FIGS. 23 and 24, an axial length of the through bore 751 of the second support portion 75 is greater than a radius of the eccentric wheel portion 53, and greater than an axial length of the waist-shaped hole 611 of the eccentric wheel mating portion 61. When the eccentric wheel portion 53 rotates, the through bore 751 can provide sufficient receiving space for eccentric rotation of the eccentric wheel portion 53 and axial movement of the eccentric wheel mating portion 61. The guiding portion 62 abuts a distal side wall and a proximal side wall of the through bore 751 of the second support portion 75 in the height direction to maintain a relatively stable positional relationship between the fixing member 7 and the articulation rod 6.

As shown in FIG. 21 and FIG. 23, a first fixing portion 71 is provided on a side of the first support portion 74 facing the driving gear 4, and a second fixing portion 44 is provided on a side of the driving gear 4 facing the fixing member 7. The first fixing portion 71 and the second fixing portion 44 form embedded connection. In this embodiment, the first fixing portion 71 is a first fixing column arranged on the first support portion 74 and convex toward the driving gear 4. The second fixing portion 44 is a cylindrical groove on the side facing the fixing member 7, and the groove is coaxially arranged with the driving gear 4. The first fixing column is at least partially in the groove, and allows the driving gear 4 to rotate relative to the first fixing portion 71. In another alternative embodiment, the first fixing portion may be a groove arranged on the side of the first support portion 74 facing the driving gear 4, and the second fixing portion may be a first fixing column arranged on the driving gear 4 and convex toward the fixing member 7, the first fixing column is coaxially arranged with the driving gear 4, and the first fixing column is at least partially embedded in the groove.

Figure 25:
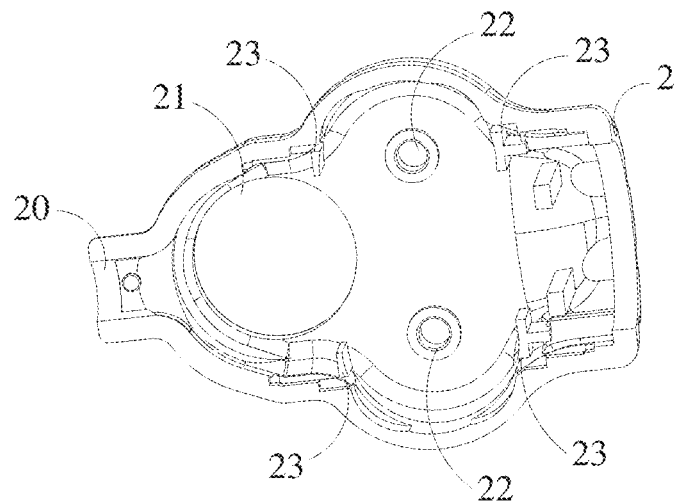
FIG. 25 is a structural schematic view of the second housing according to the second embodiment of the present disclosure.

As shown in FIGS. 25 and 27, the inner surface of the first housing 3 is provided with a first fixing hole 32, and the inner surface of the second housing 2 is provided with a second fixing hole 22. A first end 511 of the rotation shaft 51 is in the first fixing hole 32, and a second end 512 of the rotation shaft 51 is in the second fixing hole 22. The driven gear 5 is rotatable around the rotation shaft 51. The cooperation structure of the rotation shaft 51, the driven gear 5 and the housing is the same as that in the first embodiment, and are not described in detail here. The parts marked as 20 in FIG. 25 and FIG. 27 are both parts of the third channel. After the first housing 2 and the second housing 3 are combined, the two parts are combined into a complete third channel 20.

Figure 26:
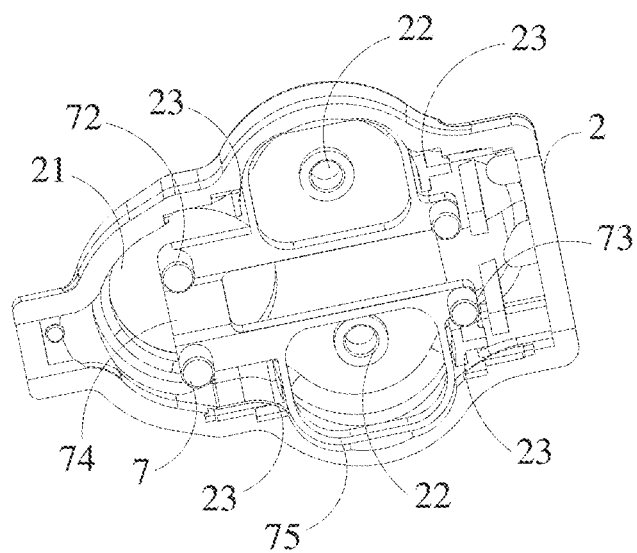
FIG. 26 is a structural schematic view of the fixing member cooperating with the second housing according to the second embodiment of the present disclosure.

As shown in FIG. 25 and FIG. 26, a receiving hole 21 is provided on the surface of the second housing 2. The articulation lever 41 passes through the receiving hole 21 and is exposed outside the second housing 2. The fixing member 7 is at least partially in the receiving cavity of the second housing 2. At least one limit member 23 is provided on the inner surface of the second housing 2. The limit member 23 is located outside the second support portion 75, and prevents the second support portion 75 from moving axially.

As shown in FIGS. 24, 27 and FIG. 28, third fixing portions 72 are provided on a side of the first support portion 74 facing the first inner surface of the housing, and fourth fixing portions 39 are provided on the first inner surface of the housing. The third fixing portion 72 and the fourth fixing portion 39 form embedded connection. In this embodiment, the third fixing portion 72 is a second fixing column convex toward the first inner surface of the housing, and the fourth fixing portion 39 is a first support base arranged on the first inner surface. A first mating hole is provided at a center portion of the first support base, and the second fixing column is least partially in the first mating hole. The third fixing portion 72 is non-rotatably connected to the fourth fixing portion 39. For example, the third fixing portion 72 and the fourth fixing portion 39 may be in interference fit. Furthermore, as the first support portion 74 is provided with two transversely arranged third fixing portions 72 and the first housing 3 is provided with two transversely arranged fourth fixing portions 39, the third fixing portions 72 are further prevented from rotating relative to the fourth fixing portions 39. In an alternative embodiment, the third fixing portion 72 may include a first mating hole, the fourth fixing portion 39 may be a fixing column convex toward the first support portion 74. In another alternative embodiment, first mating holes corresponding to the second fixing column may be directly provided on the first inner surface. In a selective embodiment, a cross section of the third fixing portion 72 is not circular, and the fourth fixing portion 39 is a fixing hole with a cross section that is also not circular. For example, a cross section of the third fixing portion 71 or the fourth fixing portion 39 is in a shape of a triangle or a polygon, to prevent the fixing member 7 from rotating relative to the housing.

As shown in FIGS. 24, 27 and FIG. 28, fifth fixing portions 73 are provided on the side of the second support portion 75 facing the first inner surface, sixth fixing portions 34 are provided on the first inner surface of the housing. The fifth fixing portion 73 and the sixth fixing portion 34 form embedded connection. In this embodiment, the fifth fixing portion 73 is a third fixing column convex toward the first inner surface, and the sixth fixing portion 34 is a second support base arranged on the first inner surface. A second mating hole is provided at a center portion of the second support base, and the third fixing column is at least partially in the second mating hole. The fifth fixing portion 73 is non-rotatably connected with the sixth fixing portion 34. For example, the fifth fixing portion 73 and the sixth fixing portion 34 may be in interference fit. Furthermore, as the fixing member 7 is provided with two transversely arranged fifth fixing portions 73 and the first housing 3 is provided with two transversely arranged sixth fixing portions 34, the fifth fixing portion 73 is further prevented from rotating relative to the sixth fixing portion 34. In an alternative embodiment, the fifth fixing portion 73 may include a second mating hole, and the sixth fixing portion 34 may be a fixing column convex toward the second support portion 75. In another alternative embodiment, second mating holes corresponding to the third fixing columns may be directly provided on the first inner surface.

FIGS. 29 to 44 show the structure of an articulation mechanism according to a third embodiment of the present disclosure. Different from the first embodiment and the second embodiment, in the third embodiment, the articulation mechanism further includes at least one locking member. When not rotated under external force, the locking portion is engaged with the driving gear teeth and/or the driven gear teeth of the gear assembly to prevent the gear assembly from rotating. Therefore, the position stability of the head assembly is improved as uncontrollable rotation of the head assembly is prevented. When the driving gear and/or the driven gear of the gear assembly is driven under external force to rotate, the locking portion moves away from the first teeth portion and/or the second teeth portion, and no longer blocks the gear assembly from rotating, so that the rotation function of the articulation mechanism is not affected.

Figure 29:
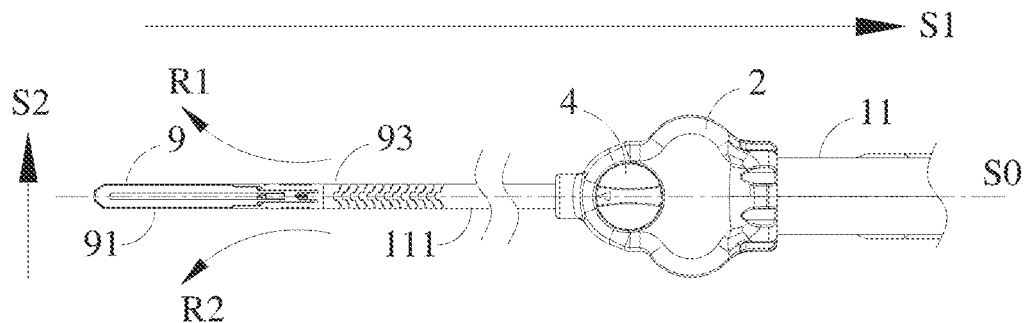
FIG. 29 is a top view of a surgical stapler according to a third embodiment of the present disclosure.
Figure 30:
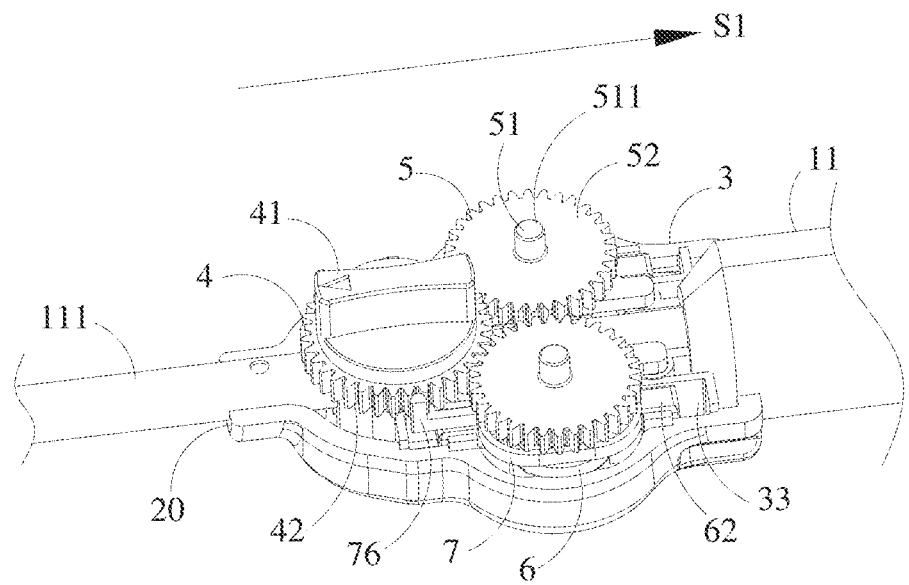
FIG. 30 is a structural schematic view of an articulation mechanism omitting a second housing and cooperating with an instrument platform of the stapler according to the third embodiment of the present disclosure.
Figure 31:
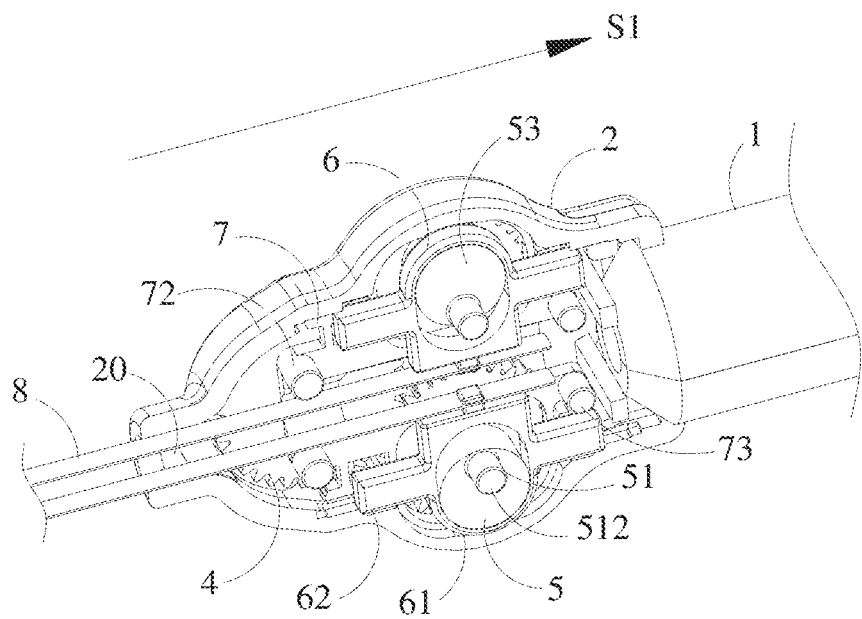
FIG. 31 is a structural schematic view of the articulation mechanism omitting a first housing and cooperating with the instrument platform of the stapler according to the third embodiment of the present disclosure.

As shown in FIGS. 29 to 31, the composition of the surgical stapler and the rotating driving principle of the articulation piece 8 to the head assembly 9 are similar to those of the first embodiment, which are described above with reference to FIGS. 1 and 2, and are not described in detail here.

Figure 32:
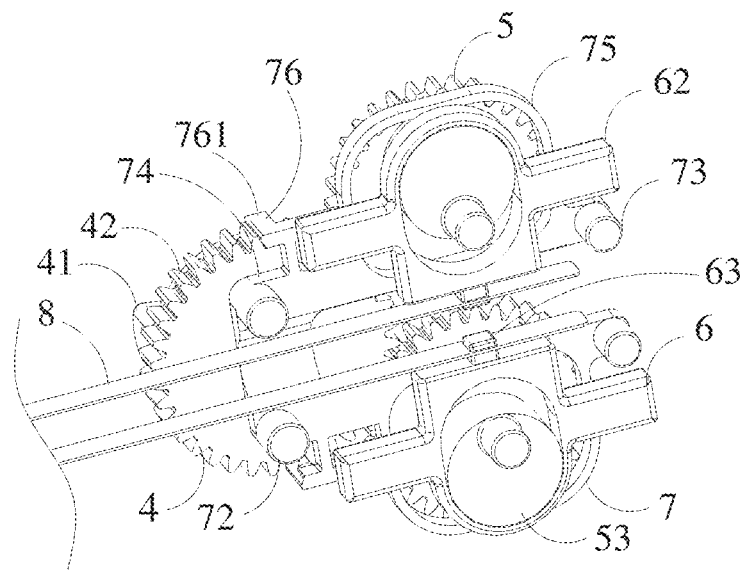
FIG. 32 is a structural schematic view of the articulation mechanism omitting a housing according to the third embodiment of the present disclosure.

In this embodiment, the articulation mechanism includes a housing having a first inner surface and a second inner surface. As shown in FIGS. 30 and 31, the housing is divided into a first housing 3 located at the bottom and a second housing 2 located at the top. A third channel 20 is formed in the first housing 3 and the second housing 2, and the elongated body 11 passes through the third channel 20. The parts marked as 20 in FIG. 31 and FIG. 32 are both parts of the third channel. After the first housing 2 and the second housing 3 are combined, the two parts are combined into a complete third channel 20. The first inner surface is the inner surface of the first housing 3, and the second inner surface is the inner surface of the second housing 2.

As shown in FIGS. 31 and 32, the articulation mechanism includes a housing, a gear assembly, a fixing portion 7 and articulation rods 6, which are received in a receiving cavity formed in a first housing 3 and a second housing 2. The housing is divided into the first housing 3 and the second housing 2. The gear assembly includes a driving gear 4 and driven gears 5. The driving gear 4 includes an operating portion and a first teeth portion 42. In this embodiment, the operating portion is an articulation lever 41 at least partially exposed outside the second housing 2. In another alternative embodiment, the driven gear 5 may include an operating portion, and the driven gear 5 is manually operated to drive the driving gear 4 to rotate. The driven gear 5 includes a second teeth portion 52, a first mating portion and a rotation shaft 51. The rotation shaft 51 passes through the second teeth portion 52 and the first mating portion. The driven gear teeth 52 is engaged with the driving gear teeth 42, so that the driven gear 5 can be driven to rotate when the driving gear 4 rotates. The articulation rod 6 includes a second mating portion and an articulation piece mating portion 63, and the articulation piece mating portion 63 is connected to a proximal end of the articulation piece 8. The second mating portion is cooperated with the first mating portion, so that when the driven gear 5 rotates, the articulation piece mating portion 63 of the articulation rod 6 is driven to move axially, and the articulation rod 6 drives the articulation piece 8 to move axially. In the present disclosure, when the driving gear 4 and the driven gear 5 rotate, the articulation rod 6 and the articulation piece 8 are driven to move axially through the cooperation between the driving gear 4, the driven gear 5, the articulation rod 6 and the articulation piece 8. By adjusting the direction and the angle of rotation of the driving gear 4, the direction and angle of rotation of the head assembly 9 can be flexibly adjusted.

As shown in FIG. 31 and FIG. 32, in this embodiment, two articulation rods 6 are provided corresponding to two articulation pieces 8, and the two articulation rods 6 are symmetrically arranged relative to the axial direction of the stapler. When the driving gear 4 rotates, the moving directions of the two articulation rods 6 are opposite. And two driven gears 5 are correspondingly provided. The relative position and cooperation structure between the driving gear 4 and the driven gear 5 are similar to those in the first embodiment and are not described in detail herein.

Figure 33:
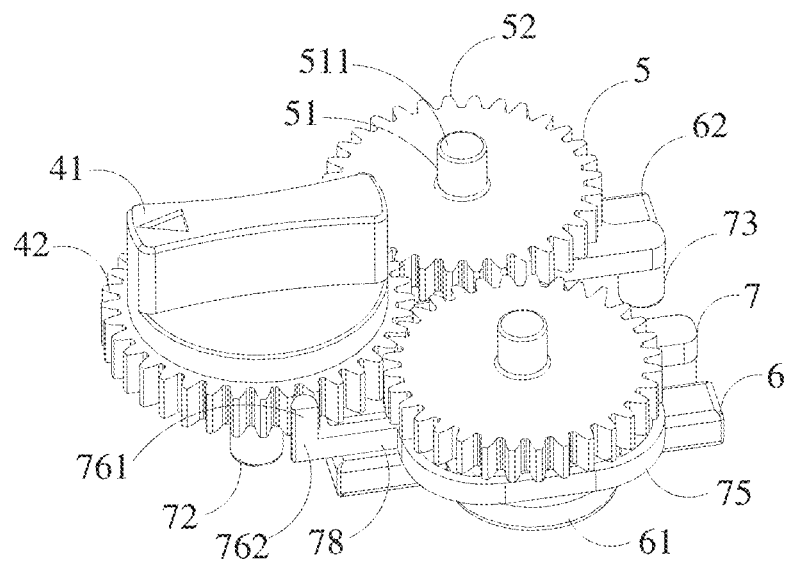
FIG. 33 is a structural schematic view of the articulation mechanism omitting the housing according to the third embodiment of the present disclosure.
Figure 34:
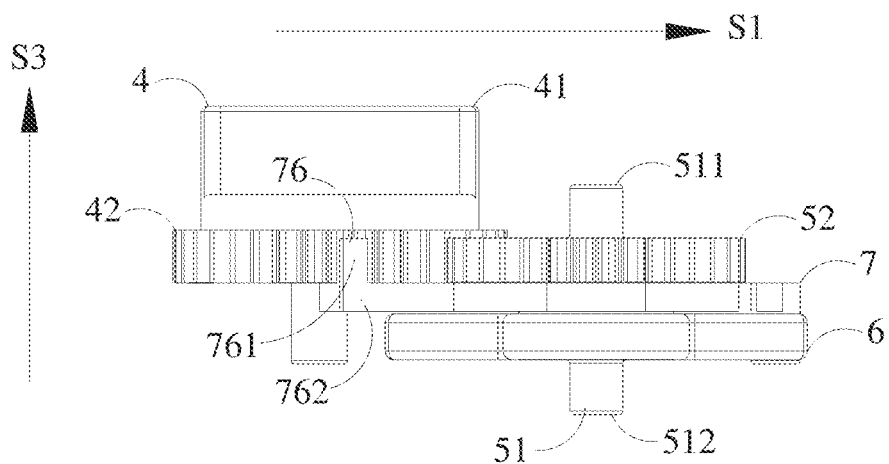
FIG. 34 is a front view of the articulation mechanism omitting the housing according to the third embodiment of the present disclosure.
Figure 35:
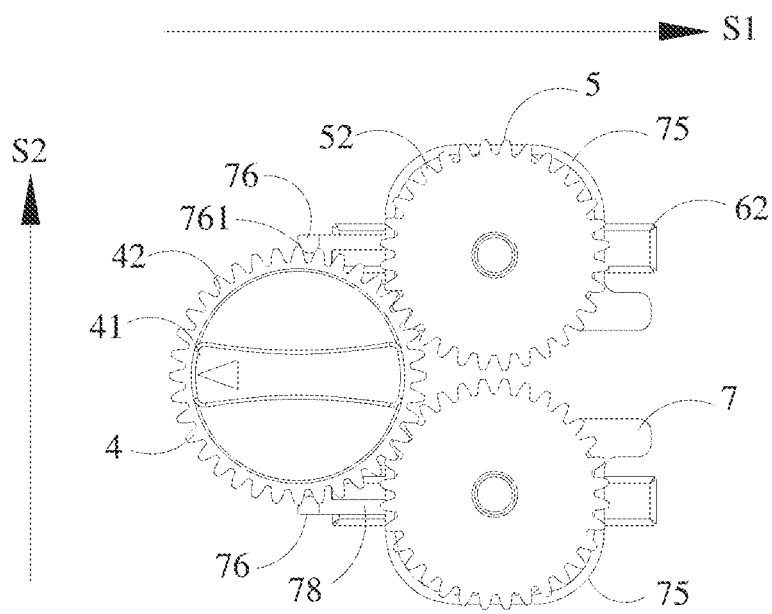
FIG. 35 is a top view of the articulation mechanism omitting the housing according to the third embodiment of the present disclosure.

As shown in FIG. 33 and FIG. 34, the first teeth portion 42 includes a plurality of driving gear teeth. The articulation mechanism further includes at least one locking member 76 having a locking portion 761. In the initial state, the locking portion 761 is engaged with the first teeth portion 42 to prevent the driving gear 4 from rotating, so that the position stability of the head assembly 9 is improved and uncontrollable rotation is prevented. When the articulation lever 41 of the driving gear 4 is operated to drive the driving gear 4 to rotate, the locking portion 761 moves away from the first teeth portion 42 under a force of the first teeth portion 42, and no longer blocks the driving gear 4 from rotating. Therefore, the articulation mechanism can still drive the head assembly 9 to rotate, and the rotation function of the articulation mechanism is not affected.

In this embodiment, the locking element 76 is at least partially elastic. In the initial state, the locking portion 761 is at least partially embedded in a space between two adjacent driving gear teeth, and the locking member 76 is not elastically deformed or only elastically deformed with a small deformation. At this time, if the driving gear 4 has an unintentional rotating tendency when the stapler is shaken, as the force applied by the driving gear tooth on the locking portion 761 is smaller than the force needed to elastically deform the locking member 76, the locking member 76 remains embedded in the space between two adjacent driving gear teeth, to block the first teeth portion 42 from rotating. When the operator rotates the articulation lever 41, the driving gear 4 has a rotating tendency under the force applied by the articulation lever 41 operated by the operator. At this time, the force applied by the driving gear tooth on the locking portion 761 is greater than the force needed to elastically deform the locking member 76. The locking portion 761 is elastically deformed under the force of the first teeth portion 42 and moves away from the first teeth portion 42, then the locking portion 761 no longer blocks the driving gear 4 from rotating. At this time, the articulation mechanism can drive the head assembly 9 to rotate. When the articulation lever 41 is free from the external force applied by the operator, the driving gear 4 stops rotating, and the locking portion 761 moves toward the first teeth portion 42 under the action of the elastic restoring force, enters the space between two adjacent driving gear teeth again, and is engaged with the first teeth portion 42 again, so that the driving gear 4 is kept at the current position without unintentional movement, and thus the head assembly 9 can be well maintained at the current angle of rotation.

As shown in FIGS. 32 to 35, in this embodiment, the articulation mechanism further includes a fixing member 7. The fixing member 7 is located between the gear assembly and the first inner surface of the housing. The gear assembly is fixed to the first inner surface of the housing through the fixing member 7. Both the driving gear 4 and the driven gear 5 are rotatable relative to the fixing member 7, so that the structural stability of the articulation mechanism is improved, unstable movement of the head assembly 9 due to instability of the gear assembly during use is prevented, and the surgical effect is improved. Specifically, the fixing member 7 includes a first support portion 74 and two second support portions 75. The first support portion 74 is located between the driving gear 4 and the first inner surface of the housing. The second support portion 75 is located between the driven gear 5 and the first inner surface of the housing. The articulation rod 6 is located between the second support portion 75 and the first inner surface of the housing. The locking member 76 further includes a connecting portion 762, and the locking portion 761 is connected to the fixing member 7 through the connecting portion 762. The fixing member 7 is fixed to the first housing 3. Therefore, the locking member 76 can be fixed to the first housing 3 through the fixing member 7. The fixing structure of the fixing member 7, the gear assembly and the first housing 3 will be described in detail below.

In this embodiment, the first mating portion is an eccentric wheel portion 53, and the second mating portion is an eccentric wheel mating portion 61 cooperated with the eccentric wheel portion 53. Therefore, when the driven gear 5 rotates, the rotational movement of the driven gear 5 is converted into the axial movement of the articulation rod 6. The selective cooperation structures of the eccentric wheel portion 53 and the eccentric wheel mating portion 61 are the same as those of the first embodiment and are not described in detail herein.

As shown in FIG. 30, guiding slots 33 extending axially are provided on the inner surface of the first housing 3. The articulation rod 6 further includes guiding portions 62. The structures of the guiding slot 33 and the guiding portion 62 and cooperation structure between the guiding slot 33 and the guiding portion 62 are the same as those in the first embodiment, and are not described in detail here. As shown in FIG. 32, in this embodiment, the structure, cooperation structure and alternative embodiments of the eccentric wheel mating portion 61, the articulation piece mating portion 63 and the articulation piece 8 are the same as those of the first embodiment and are not be described in detail here.

In the third embodiment, the working principle of the articulation mechanism driving the head assembly to rotate in the direction R1 or direction R2 relative to the instrument platform can be referred to the working principle description of the first embodiment with reference to FIGS. 13 to 16, and are not be described in detail here.

The structures of the locking member 76 and the fixing member 7 of the third embodiment will be described in detail below with reference to FIGS. 36 to 39.

Figure 36:
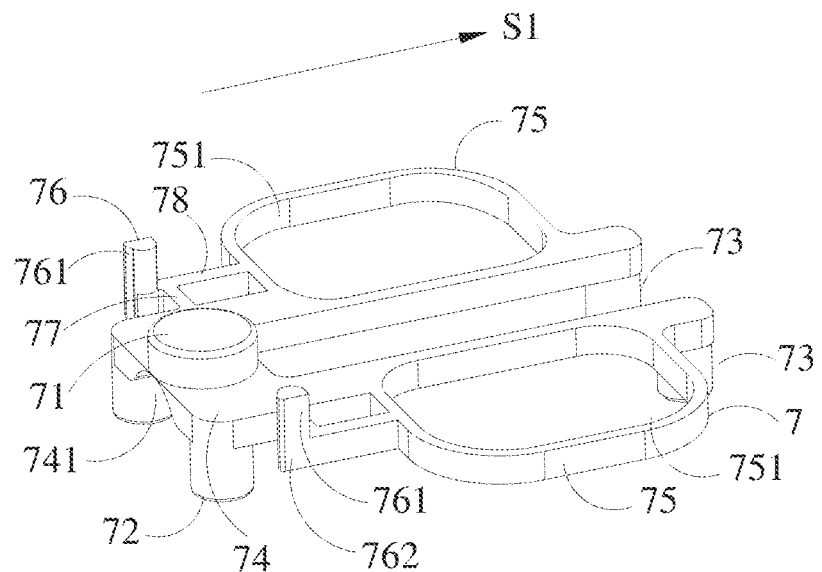
FIG. 36 and FIG. 37 are structural schematic views of a fixing member according to the third embodiment of the present disclosure.
Figure 37:
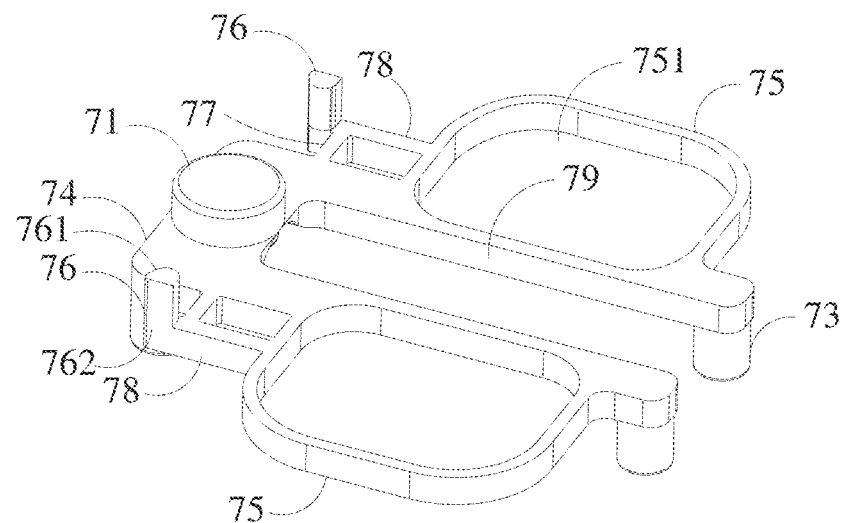

As shown in FIG. 36 and FIG. 37, the locking member 76 is rod-shaped and extending parallel to the central axis of the driving gear 4. The fixing member 7 includes two second support portions 75. A second channel 79 extending axially is formed between the two second support portions 75, and a proximal end of the elongated body passes through the second channel 79. The fixing member 7 is provided with two locking members 76 symmetrically arranged relative to the axis of the stapler. The two locking members 76 are respectively arranged between the two second support portions 75 and the first support portion 74. The connecting portion 762 of each locking member 76 is connected to the first support portion 74 through a first connecting arm 77, and is connected to one of the second support portions 75 through a second connecting arm 78. As the locking member 76 is fixed between the first support portion 74 and the second support portion 75 through the first connecting arm 77 and the second connecting arm 78, the stability of the locking member 76 fixing to the fixing member 7 can be improved. In an embodiment, the locking member 76, the first connecting arm 77, and the second connecting arm 78 may be integrally formed with the first support portion 74 and the second support portion 75. In another alternative embodiment, the first connecting arm 77 and the second connecting arm 78 may be connected to the first support portion 74 and the second support portion 75 through welding. In another alternative embodiment, the first connecting arm 77 and the second connecting arm 78 may be integrally formed with the first support portion 74 and the second support portion 75, and further integrally formed with the connecting portion 762 of the locking member 76.

Figure 38:
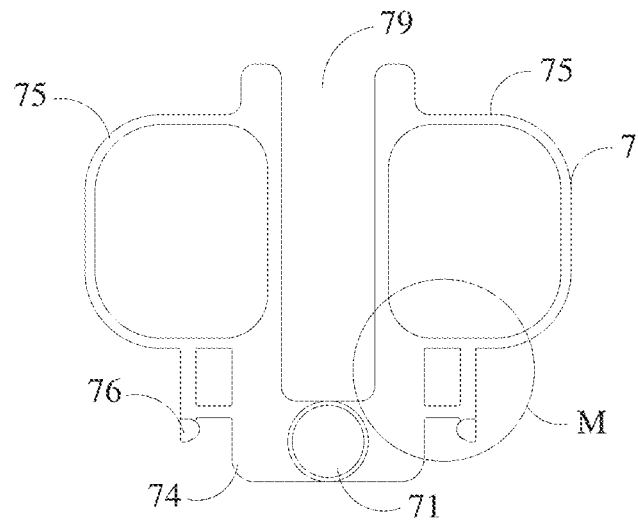
FIG. 38 is a top view of the fixing member according to the third embodiment of the present disclosure.
Figure 39:
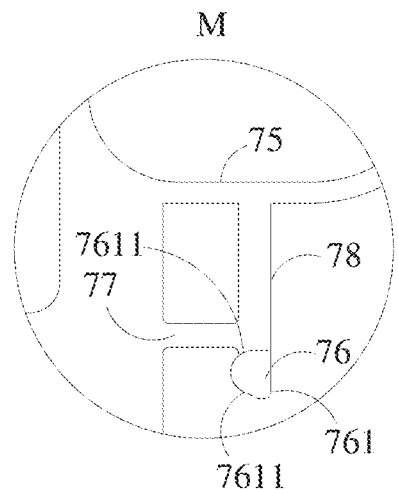
FIG. 39 is an enlarged view of M area in FIG. 38.

As shown in FIGS. 38 and 39, in this embodiment, the first connecting arm 77 is perpendicular to the second connecting arm 78. Therefore, when the locking member 76 is elastically deformed by the tooth of the driving gear 4, an end of the connecting portion 762 of the locking member 76 is maintained at a stable position by the first connecting arm 77 and the second connecting arm 78, and is prevented from moving axially and laterally.

As shown in FIG. 39, in this embodiment, the locking portion 761 includes two inclined guiding surfaces 7611. When the locking portion 761 is engaged with the first teeth portion 42 of the driving gear 4, the guiding surface 7611 of the locking portion 761 is at least partially in a space between two adjacent teeth of the driving gear 4, and the two guiding surfaces 7611 are respectively relative to side surfaces of the two adjacent teeth of the driving gear 4. When the operator operates the articulation lever to rotate the driving gear 4, the tooth of the driving gear 4 applies a force on the guiding surface 7611, and the force is decomposed by the guiding surface 7611 to obtain a force driving the locking portion 761 away from the driving gear 4, and the guiding surface 7611 can better guide the locking portion 761 to separate from the first teeth portion 42.

In another alternative embodiment, a side of the locking portion 761 facing the first teeth portion 42 is an integral arc surface. When the locking portion 761 is engaged with the first teeth portion 42, the arc surface of the locking portion 761 is at least partially in the space between two adjacent teeth of the driving gear 4. When the operator operates the articulation lever to rotate the driving gear 4, the tooth of the driving gear 4 applies a force on the guiding surface 7611, and the force is decomposed by the arc surface to obtain a force driving the locking portion 761 away from the driving gear 4, and the arc surface can better guide the locking portion 761 to separate from the first teeth portion 42.

Figure 40:
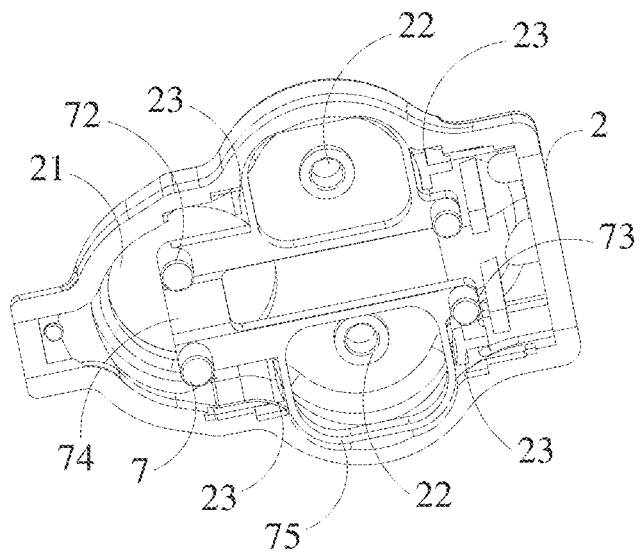
FIG. 40 is a structural schematic view of the fixing member cooperating with the second housing according to the third embodiment of the present disclosure.
Figure 41:
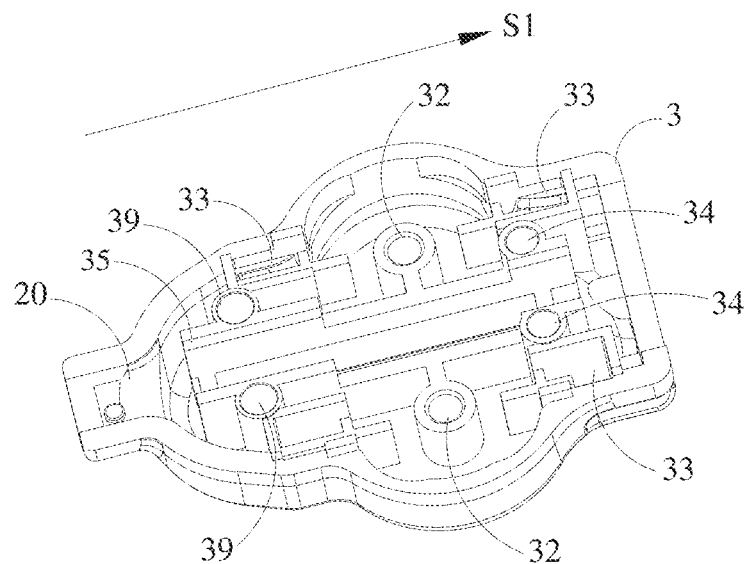
FIG. 41 is a structural schematic view of the first housing according to the third embodiment of the present disclosure.

The cooperation structure between the fixing member 7 and other members of the present disclosure is described in detail below with reference to FIGS. 40 to 42. As shown in FIGS. 40 and 41, the inner surface of the first housing 3 is provided with a first fixing hole 31, and the inner surface of the second housing 2 is provided with a second fixing hole 22. The first end 511 of the rotation shaft 51 is in the first hole, and the second end 512 of the rotation shaft 51 is in the second fixing hole 22. The driven gear 5 is rotatable around the rotation shaft 51. The cooperation structure of the driven gear 5, the rotation shaft 51 and the housing is the same as that of the first embodiment, and are not be described in detail here.

As shown in FIG. 40, a receiving hole 21 is provided on the surface of the second housing 2. The articulation lever 41 passes through the receiving hole 21 and is exposed outside the second housing 2. The fixing member 7 is at least partially in the receiving cavity of the second housing 2. At least one limit member 23 is disposed on the inner surface of the second housing 2. The limit member 23 is outside the second support portion 75, and the limit member 23 prevents the second support portion 75 from moving axially.

Figure 42:
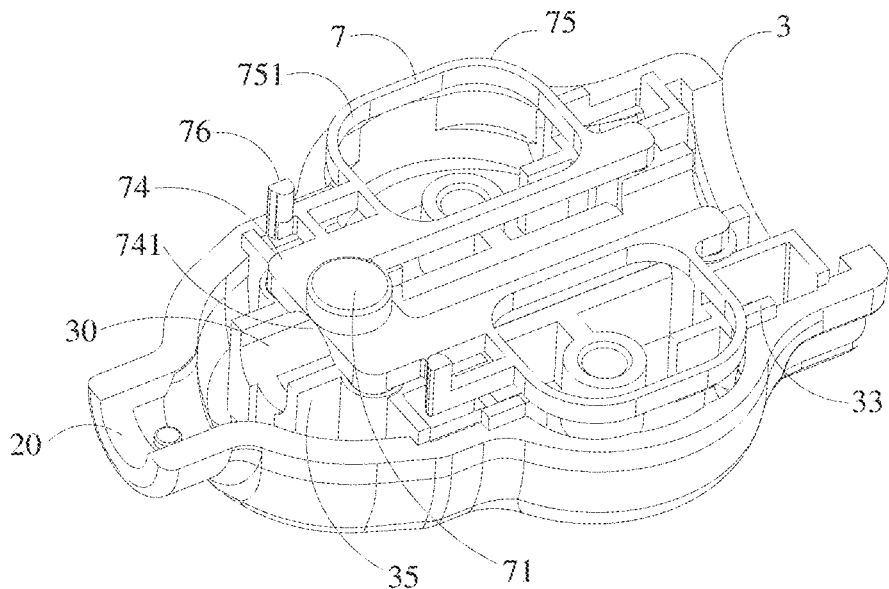
FIG. 42 is a structural schematic view of the fixing member cooperating with the first housing according to the third embodiment of the present disclosure.

As shown in FIGS. 41 and 42, a receiving groove 741 is provided on a side of the inner surface of the first support portion 74 facing the first housing 3, and a limit portion 35 is provided on the inner surface of the first housing 3 at a position corresponding to the receiving groove 741. The receiving groove 741 and the limit portion 35 form a first channel 30 extending axially, and the elongated body jacketed on the articulation piece 8 passes through the first channel 30. A surface of the receiving groove 741 is selectively an arc surface, and a surface of the limit portion 35 is also selectively an arc surface. Therefore, the first channel 30 is cylindrical to better fit the outer surface of the cylindrical elongated body and better support the elongated body.

As shown in FIGS. 40 to 42, a third fixing portion 72 is provided on a side of the first support portion 74 facing the first inner surface of the housing, and a fourth fixing portion 39 is provided on the first inner surface of the housing. The third fixing portion 72 and the fourth fixing portion 39 form embedded connection. The cooperation structure and alternative embodiments of the third fixing portion 72 and the fourth fixing portion 39 are the same as those of the parts with the same reference numerals in the second embodiment and are not described in detail here.

As shown in FIGS. 40 to 42, a fifth fixing portion 73 is provided on a side of the second support portion 75 facing the first inner surface of the housing, and a sixth fixing portion 34 is provided on the first inner surface of the housing. The fifth fixing portion 73 and the sixth fixing portion 34 form embedded connection. The cooperation structure and alternative embodiments of the fifth fixing portion 73 and the sixth fixing portion 34 are the same as those in the second embodiment and are not described in detail here.

As shown in FIG. 42, a first fixing portion 71 is provided on a side of the first support portion 74 facing the driving gear 4, and a second fixing portion 44 is provided on a side of the driving gear 4 facing the fixing member 7 (shown in FIG. 21). The first fixing portion 71 and the second fixing portion 44 form embedded connection. The cooperation structure and alternative embodiments of the first fixing portion 71 and the second fixing portion 44 are the same as those in the second embodiment and are not described in detail here.

Figure 43:
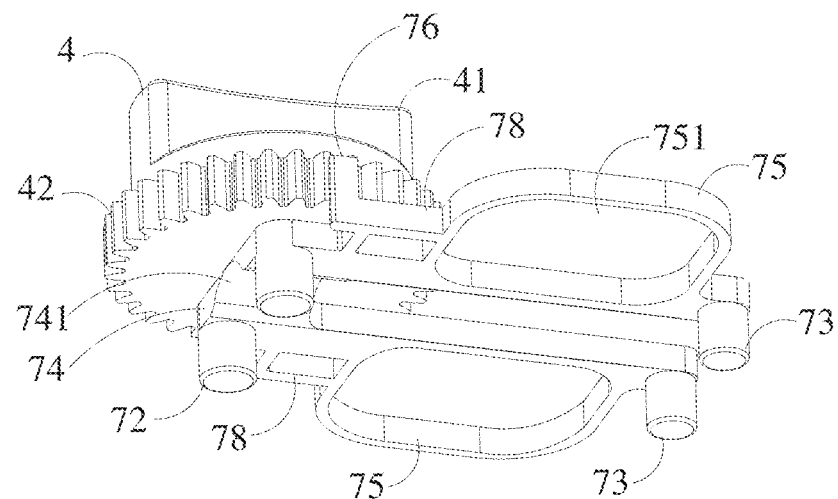
FIG. 43 is a structural schematic view of the fixing member cooperating with the driving gear according to the third embodiment of the present disclosure.
Figure 44:
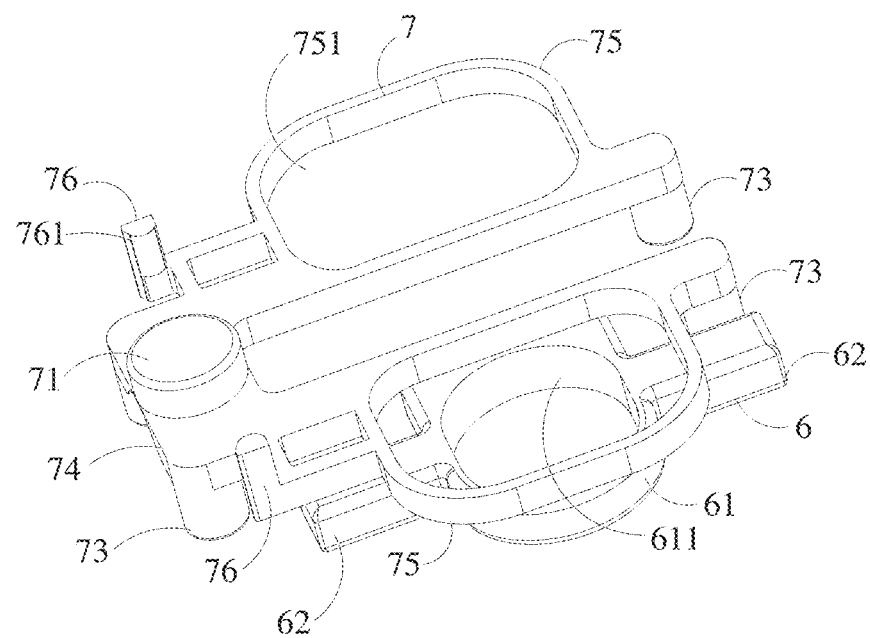
FIG. 44 is a structural schematic view of the fixing member cooperating with the articulation rod according to the third embodiment of the present disclosure.

As shown in FIG. 33 and FIGS. 43 to 44, the second support portion 75 of the fixing member 7 is provided with a through bore 751. The rotation shaft 51 of the driven gear 5 passes through the through bore 751. The eccentric wheel portion 53 of the driven gear 5 passes through the through bore 751 and cooperates with the eccentric wheel mating portion 61 of the articulation rod 6. As shown in FIG. 44, am axial length of the through bore 751 of the second support portion 75 is greater than a radius of the eccentric wheel portion 53, and greater than an axial length of the waist-shaped hole 611 of the eccentric wheel mating portion 61. When the eccentric wheel portion 53 rotates, the through bore 751 can provide sufficient receiving space for the eccentric rotation of the eccentric wheel portion 53 and the axial movement of the eccentric wheel mating portion 61. The guiding portion 62 abuts the distal side wall and the proximal side wall of the through bore 751 of the second support portion 75 in a longitudinal direction to keep the fixing member 7 at a relatively stable position relative to the articulation rod 6.

Figure 45:
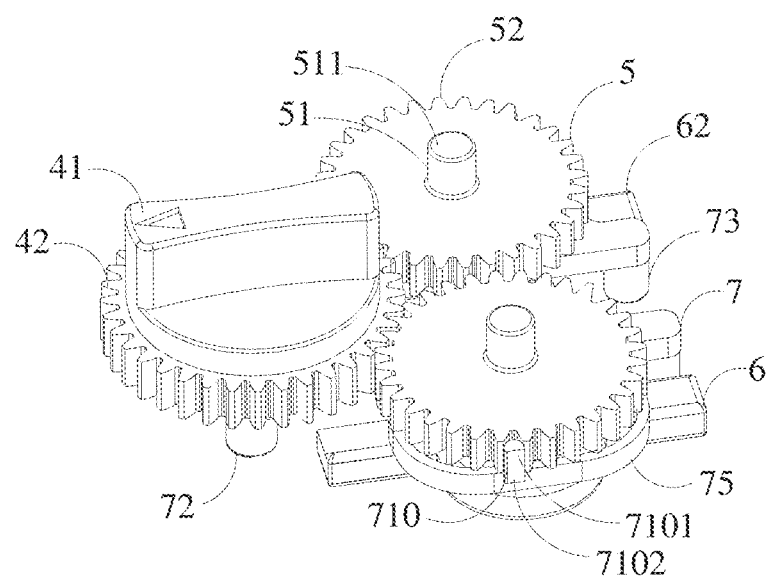
FIG. 45 is a structural schematic view of a fixing member cooperating with a gear assembly according to a fourth embodiment of the present disclosure.

The above embodiment is described by taking the structure of the locking member being engaged with the driving gear in the gear assembly as an example. In a fourth embodiment shown in FIG. 45, a locking member 710 engaged with the driven gear 5 of the gear assembly is provided. The locking member 710 includes a locking portion 7101 and a connecting portion 7102. The connecting portion 7102 is connected to the first support portion 74 and/or the second support portion 75. As shown in FIG. 45, when the driving gear 4 and/or the driven gear 5 are not under external force, the locking portion 7101 of the locking member 710 is engaged with the second teeth portion 52 to block the driven gear 5 from rotating. When the driving gear and/or the driven gear are driven to rotate under external force, the locking portion 7101 moves away from the second teeth portion 52 under the force of the second teeth portion 52, and no longer blocks the driven gear 52 from rotating. The number of the locking member 710 may be one, two, or more, and the locking member 710 may be engaged with only one driven gear 5 or may be engaged with two driven gears 5 respectively.

In this embodiment, the locking member 710 is at least partially elastic. When the driving gear 4 and/or the driven gear 5 are driven to rotate under external force, the locking portion 7101 is elastically deformed by the second teeth portion 52 and moves away from the second teeth portion 52. When the driven gear 5 stops rotating, the locking portion 52 is engaged with the second teeth portion 52 under the action of the elastic restoring force again.

In this embodiment, the second teeth portion 52 includes a plurality of driven gear teeth, and the locking portion 7101 includes two inclined guiding surfaces or an arc surface. When the locking portion 7101 is engaged with the second teeth portion 52, the guiding surface or the arc surface of the locking portion 7101 is at least partially in a space between two adjacent driven gear teeth, and the two guiding surfaces are respectively relative to side surfaces of the two adjacent driven gear teeth, or the arc surface is relative to the side surfaces of the driven gear teeth.

The structures of other members of this embodiment are the same as those of the third embodiment and are not described in detail here.

In another alternative embodiment, the locking member 76 of the third embodiment and the locking member 7101 of the fourth embodiment may be both provided, that is, the locking members cooperate with both the driving gear 4 and the driven gear 5. The alternative embodiment is also within the protection scope of the present disclosure.

In the above embodiments, the connecting portions of the locking members are all connected to the fixing members. In other alternative embodiments, the connecting portion of the locking member may be connected to other structures. For example, the connecting portion of the locking member may be directly connected to the inner surface of the housing, or connected to another member fixed to the housing.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. An articulation mechanism used for a surgical stapler, comprising:
    a gear assembly comprising a driving gear and at least one driven gear, wherein the driving gear comprises a first teeth portion, and the driven gear comprises a second teeth portion configured to be engaged with the first teeth portion and a first mating portion;
    at least one articulation rod comprising a second mating portion and an articulation piece mating portion, wherein the second mating portion is configured to cooperate with the first mating portion, so that when the driven gear rotates, the driven gear drives the articulation piece mating portion of the articulation rod to move in an axial direction of the stapler; and
    at least one articulation piece configured to extend in the axial direction and be connected to the articulation piece mating portion of the articulation rod.

2. The articulation mechanism of claim 1, further comprising a housing configured to receive the gear assembly; wherein one of a first inner surface of the housing and the driving gear is provided with a support portion, and the other is provided with a sliding slot; the support portion is configured to be rotatably located in the sliding slot.

3. The articulation mechanism of claim 1, further comprising a housing configured to receive the gear assembly; wherein the driven gear further comprises a third mating portion, and an inner surface of the housing is provided with a fourth mating portion configured to cooperate with the third mating portion, so that the driven gear is rotatable relative to the housing.

4. The articulation mechanism of claim 3, wherein the first mating portion is an eccentric wheel portion, and the second mating portion is provided with a fifth mating portion; the eccentric wheel portion is configured to be at least partially located in the fifth mating portion.

5. The articulation mechanism of claim 4, further comprising two driven gears, two articulation rods and two articulation pieces; wherein the two articulation rods are symmetrically arranged relative to the axial direction, and each of the two articulation rods is respectively connected to one of the two articulation pieces; when the driving gear rotates, the two articulation rods move in opposite directions.

6. The articulation mechanism of claim 5, wherein in an initial state, a central axis of the eccentric wheel portion of each driven gear is configured to be located outside or inside of the rotation shaft of corresponding driven gear.

7. The articulation mechanism of claim 5, wherein the driven gear is configured to be located at a proximal side of the driving gear.

8. The articulation mechanism of claim 5, wherein the rotation shaft of each driven gear is parallel to a central axis of the driving gear; a distance from the rotation shaft of one driven gear to the central axis of the driving gear is the same as a distance from the rotation shaft of the other driven gear to the central axis of the driving gear.

9. The articulation mechanism of claim 1, further comprising:
    a housing comprising a first inner surface and a second inner surface, wherein a receiving cavity is configured to be formed between the first inner surface and the second inner surface; and
    a fixing member configured to be fixedly located in the receiving cavity; wherein the fixing member comprises a third surface facing the first inner surface and a fourth surface facing the second inner surface; the gear assembly is configured to be at least partially located between the fourth surface and the second inner surface of the housing, and the gear assembly is rotatable relative to the fixing member.

10. The articulation mechanism of claim 9, wherein a first fixing portion is provided on a side of the fixing member facing the driving gear, and a second fixing portion is provided on a side of the driving gear facing the fixing member; the first fixing portion and the second fixing portion are configured to form embedded connection, and the driving gear is rotatable relative to the first fixing portion;
    the driving gear further comprises an operating portion configured to be located on a side of the first teeth portion facing the second inner surface of the housing; the first fixing portion is provided on a side of the first teeth portion facing the first inner surface of the housing;
    the first mating portion is configured to be located on a side of the second teeth portion facing the first inner surface of the housing;
    the first teeth portion and the second teeth portion are configured to be located between the fourth surface and the second inner surface of the housing; and
    the articulation rod is configured to be located between the third surface of the fixing member and the first inner surface of the housing; the fixing member is provided with a through bore, and the first mating portion of the driven gear is configured to pass through the through bore to be engaged with the second mating portion of the articulation rod.

11. The articulation mechanism of claim 9, wherein the fixing member comprises a first support portion for the driving gear; at least a part of the first support portion and at least a part of the first inner surface of the housing form embedded connection; and/or,
    the fixing member comprises at least one second support portion for the driven gear; at least a part of the second support portion and at least a part of the first inner surface of the housing form embedded connection.

12. The articulation mechanism of claim 9, wherein a receiving groove is provided on a side of the fixing member facing the first inner surface of the housing, and a limit portion is provided at a position of the housing relative to the receiving groove; the receiving groove and the limit portion are configured to enclose a channel in the axial direction for receiving an elongated body.

13. The articulation mechanism of claim 9, wherein the gear assembly comprises two driven gears, the fixing member comprises two support portions configured to respectively support the two driven gears, and a channel configured to extend in the axial direction is formed between the two support portions.

14. The articulation mechanism of claim 13, wherein the second inner surface is provided with at least one limit member, and the limit member is configured to block movement of the support portions in the axial direction.

15. The articulation mechanism of claim 1, further comprising at least one locking member provided with a locking portion; wherein when the gear assembly is not under external force, the locking portion is engaged with the gear assembly to block the driving gear and/or the driven gear from rotating, and when the gear assembly is driven to rotate under external force, the gear assembly drives the locking portion to move away from the gear assembly, so that the locking portion no longer blocks the gear assembly from rotating, at least a part of the locking member is elastic.

16. The articulation mechanism of claim 15, wherein the first teeth portion comprises a plurality of driving gear teeth, the locking portion comprises two inclined guiding surfaces or an arc surface; when the locking portion is engaged with the first teeth portion, the guiding surfaces or the arc surface of the locking portion are at least partially in a space between two adjacent driving gear teeth;

or, the second teeth portion comprises a plurality of driven gear teeth, the locking portion comprises two inclined guiding surfaces or an arc surface; when the locking portion is engaged with the second teeth portion, the guiding surfaces of the locking portion are at least partially in a space between two adjacent driven gear teeth, and the two guiding surfaces are respectively located relative to side surfaces of the two adjacent driven gear teeth, or the arc surface of the locking portion is at least partially in a space between two adjacent driven gear teeth.

17. The articulation mechanism of claim 15, wherein the locking member is a rod configured to extend parallel to a central axis of the driving gear and/or a central axis of the driven gear.

18. The articulation mechanism of claim 15, further comprising a housing and a fixing member, wherein the housing comprises a receiving cavity configured to receive the gear assembly, the fixing member and the articulation rod; the gear assembly is fixed to the housing through the fixing member; the fixing member comprises a first support portion for the driving gear and at least one second support portion for the driven gear, the first support portion is configured to be located between the driving gear and a first inner surface of the housing, the second support portion is configured to be located between the driven gear and the first inner surface of the housing;

the locking member further comprises a connecting portion, and at least a part of the locking portion is configured to be connected to the first support portion and/or the second support portion through the connecting portion.

19. The articulation mechanism of claim 18, further comprising two locking members; wherein the gear assembly comprises two driven gears, the two locking members are respectively arranged between two second support portions and the first support portion; the connecting portion of each locking member is configured to be connected to the first support portion through a first connecting arm; the connecting portion of each locking member is configured to be connected to one second support portion through a second connecting arm.

20. A surgical staple comprising the articulation mechanism according to claim 1.

* * * * *